(12) United States Patent
Groeger et al.

(10) Patent No.: US 8,105,806 B2
(45) Date of Patent: Jan. 31, 2012

(54) PROCESS FOR PREPARING OPTICALLY ACTIVE AMINO ACIDS USING A WHOLE-CELL CATALYST

(75) Inventors: Harald Groeger, Hanau (DE); Helge Werner, Bruchkoebel (DE); Josef Altenbuchner, Nutringen (DE); Anne Menzel, Sindelfingen (DE); Werner Hummel, Titz (DE)

(73) Assignee: Evonik Degussa GmbH, Essen (DE)

( * ) Notice: Subject to any disclaimer, the term of this patent is extended or adjusted under 35 U.S.C. 154(b) by 1031 days.

(21) Appl. No.: 10/593,567

(22) PCT Filed: Mar. 18, 2005
(Under 37 CFR 1.47)

(86) PCT No.: PCT/EP2005/002933
§ 371 (c)(1),
(2), (4) Date: Aug. 21, 2007

(87) PCT Pub. No.: WO2005/093081
PCT Pub. Date: Oct. 6, 2005

(65) Prior Publication Data
US 2009/0087885 A1      Apr. 2, 2009

(30) Foreign Application Priority Data
Mar. 22, 2004  (DE) .......................... 10 2004 014 280

(51) Int. Cl.
*C12P 13/04*     (2006.01)
*A01N 63/00*     (2006.01)
*A61K 38/44*     (2006.01)
(52) U.S. Cl. ...................... 435/106; 424/93.2; 424/94.4
(58) Field of Classification Search .................. None
See application file for complete search history.

(56) References Cited

U.S. PATENT DOCUMENTS

2002/0064847 A1 * 5/2002 Yamamoto et al. ........... 435/190
2006/0216801 A1   9/2006 Groger et al.

FOREIGN PATENT DOCUMENTS

JP          62-000289        1/1987

OTHER PUBLICATIONS

Hong, Biotechnol. Bioeng., 1986, 28: 1421-1431.*
Smith et al., J. Biol. Chem., 1993, 268: 10746-10753.*
Neuhauser et al., Biotechnol. Bioeng., 1998, 60: 277-282.*
U.S. Appl. No. 10/508,702, filed Jul. 11, 2005, Hummel, et al.
Andrey Galkin, et al., "Synthesis of Optically Active Amino Acids from α-Keto Acids with *Escherichia coli* Cells Expressing Heterologous Genes", Applied and Environmental Microbiology, XP-002079513, vol. 63, No. 12, Dec. 1997, pp. 4651-4656.
Japanese Office Action dated Apr. 7, 2011 as received in the corresponding Japanese Application No. 2007-504327.

* cited by examiner

*Primary Examiner* — Ileana Popa
(74) *Attorney, Agent, or Firm* — Oblon, Spivak, McClelland, Maier & Neustadt, L.L.P.

(57) ABSTRACT

The present invention relates to a process for preparing, in particular, enantiomerically enriched L-α-amino acids, in particular those of the general formula (I). In this connection, the process according to the invention uses 2-ketocarboxylic acids which are converted into the desired products using a whole-cell catalyst which comprises an amino acid dehydrogenase and a cofactor-regenerating enzyme.

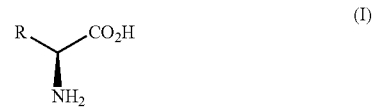

(I)

16 Claims, 6 Drawing Sheets

PROCESS FOR PREPARING OPTICALLY ACTIVE AMINO ACIDS USING A WHOLE-CELL CATALYST

CROSS-REFERENCE TO RELATED APPLICATIONS

Figure 1:
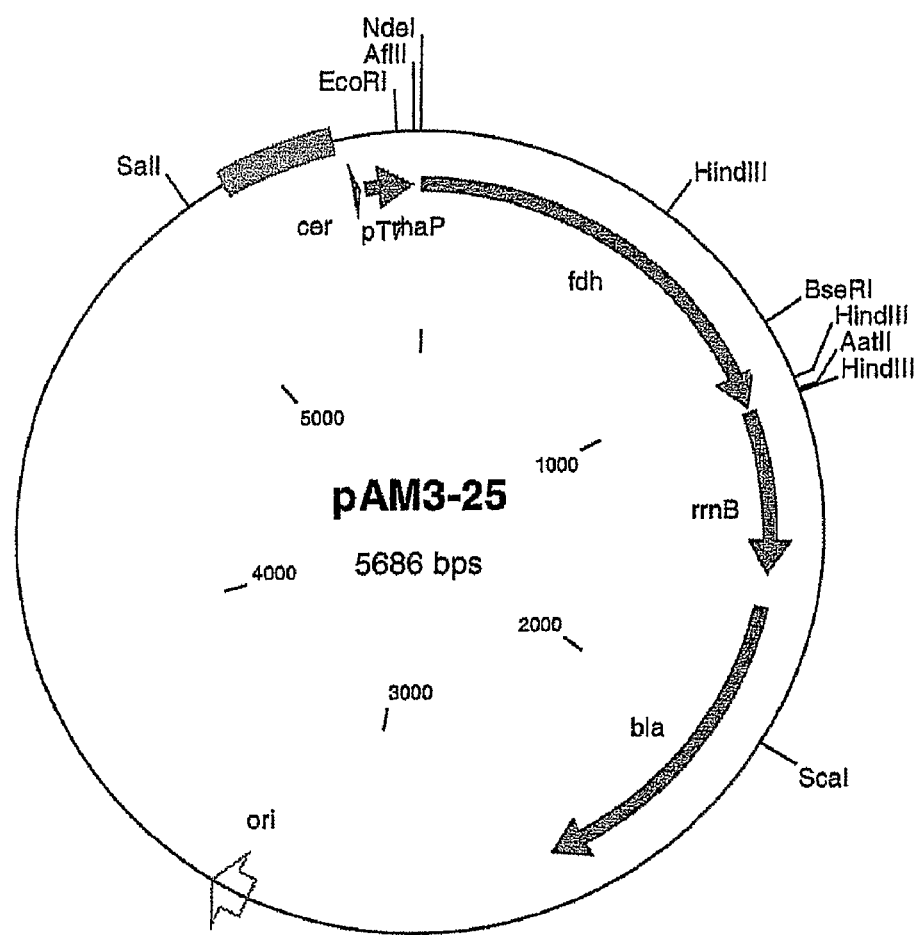

The present application is a 35 U.S.C. §371 National Stage patent application of International patent application PCT/EP05/002933, filed on Mar. 18, 2005, which claims priority to German patent application DE 102004014280.7, filed on Mar. 22, 2004.

The invention describes a process for preparing optically active L-α-amino acids. In particular the present invention describes a process for preparing compounds of the general formula (I)

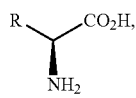

in which R is alkyl, in particular a space-filling branched alkyl group which exhibits a tertiary C atom and which possesses 5-10 C atoms, for example tert-butyl, and substituted alkyl, or salts which are derived therefrom.

Optically active L-α-amino acids are used for preparing a number of valuable compounds. For example, these compounds function as intermediates in the production of pharmaceuticals. L-tert-Leucine, which can be found as a structural element in a number of pharmaceutical active compounds and is consequently required as an intermediate for synthesizing the corresponding pharmaceutical active compounds, is a particularly valuable representative of this product class. A. S. Bommarius et al., (J. Mol. Cat. B: Enzymatic 1998, 5, 1-11) provides examples of uses of L-tert-leucine as a building block for pharmaceutical active compounds.

Using a leucine dehydrogenase and a formate dehydrogenase from *Candida boidinii* to enzymically reduce 2-ketocarboxylic acids while regenerating cofactor in situ constitutes an industrially established method for preparing optically active L-α-amino acids. In particular, this route is suitable for preparing the non-proteinogenic amino acid L-tert-leucine, which is produced on the ton scale using this biocatalytic method. The method is described in detail in the literature (EP0692538; U. Kragl, D. Vasic-Racki, C. Wandrey, Bioprocess Engineering 1996, 14, 291-297; A. S. Bommarius, M. Schwarm, K. Drauz, J. Mol. Cat. B: Enzymatic 1998, 5, 1-11; G. Krix, A. S.: Bommarius, K. Kottenhahn, M. Schwarm, M.-R. Kula, J. Biotechnol. 1997, 53, 29-39, A. Liese, C. Wandrey, A. Liese, K. Seelbach, C. Wandrey, Industrial Biotransformations, Wiley-VCH, Weinheim, 2000, p. 125f. and A. S. Bommarius, K. Drauz, W. Hummel, M.-R. Kula, C. Wandrey, Biocatalysis 1994, 10, 37-47. In addition, a general review is provided in A. S. Bommarius in: Enzyme Catalysis in Organic Synthesis (Eds.: K. Drauz and H. Waldmann), Volume 2, 2nd edition, Wiley-VCH, Weinheim, 2003, chapter 15.3, p. 1047f.).

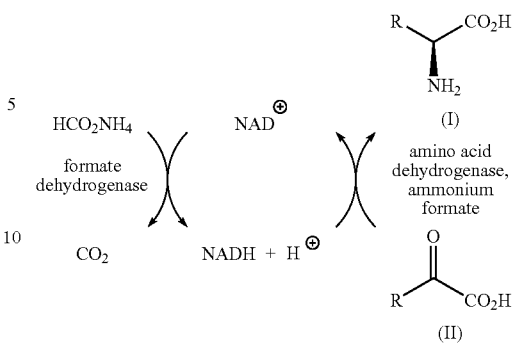

Scheme 1. Preparation of L-tert-leucine using isolated enzymes and added cofactor (taking as an example an $NAD^+$-dependent amino acid dehydrogenase and a formate dehydrogenase for regenerating cofactor)

Typical quantities of NAD+ cofactor which are used, and which have to be added, are described, for example, in EP0692538 and are in the range of from 0.0008 equivalents to 0.02 equivalents. In addition, G. Krix et al. (J. Biotechnol. 1997, 53, 29-39) describe the preparation of (S)-neopentylglycine in industrial batch sizes using an $NAD^+$ cofactor quantity of 0.003 equivalents. Typical substrate concentrations in EP0692538 are 100-250 mM. A. Liese et al. (Industrial Biotransformations, Wiley-VCH, Weinheim, 2000, p. 125f.) describe the preparation of L-tert-leucine using a substrate concentration of 0.5 M and with a yield of 74%. G. Krix et al. (J. Biotechnol. 1997, 53, 29-39) also describe the performance of reductive aminations using isolated leucine dehydrogenase and formate dehydrogenase enzymes at substrate concentrations of from 0.5 to 1 M.

The high turnovers and outstanding enantioselectivities, which are >99% ee and consequently help to meet the strict quality demands placed on pharmaceutical intermediates, are advantageous features of this method. It is also possible to operate at high substrate concentrations, something which is an important aspect particularly from the industrial point of view.

However, a disadvantage of the previous method is, in the first place, the requirement for isolated enzymes. These latter are used, in particular, in purified form, with this being accompanied by an increase in the share of the costs due to the biocatalyst. Because of the high enzyme costs resulting from this, it is necessary to recycle the enzymes many times in order to obtain a favorable process economy, in particular low enzyme costs. In addition to the long running times of these recycling procedures, which are advantageously carried out continuously, the relatively small reaction volumes per batch which result from this are disadvantageous.

Another disadvantage is the requirement for cofactor which is added in the reaction. While these cofactors are added catalytically in orders of size of approx. 0.001 equivalents, they nevertheless represent, because of their high price, a considerable cost factor even at catalytic quantities.

A process in which the necessity of using isolated enzymes and of adding cofactor is dispensed with, or the addition of cofactor is kept to a minimum, and the synthesis nevertheless proceeds with a high turnover rate, high enantioselectivity and high volumetric productivity, would therefore be desirable. In this way, it would be possible to lower enzyme costs considerably and save on cofactor costs, and consequently increase the economy of the process.

Soda et al. describe the use of a whole-cell catalyst, comprising a leucine dehydrogenase and a bacterial formate dehydrogenase, in the reductive amination of, inter alia, branched-chain α-ketocarboxylic acids such as L-tert-leucine (Appl. Environm. Microbiology 1997, 63, 4651-4656). This publication explicitly points out that the enzymes which are required in the reductive amination can be used in the form of a whole-cell catalyst, in particular *E. coli*, as live or resting cells, which comprises these enzymes. However, if preference were to be given to taking advantage of the intracellular pool of NAD⁺ in *E. coli*, for the purpose of avoiding having to add the NAD⁺, the final concentration of product would then be restricted to about 0.3 M. This is not adequate for industrial applications.

The object of the present invention was therefore to specify another process for preparing L-α-amino acids which operates enzymically and which can be carried out advantageously on an industrial scale. The process should, in particular, be superior to the processes of the prior art with the above described aspects and should make it possible to produce the desired products advantageously from the point of view of process economics (in particular space-time yield).

These objects, and other objects which are not specified in more detail but which ensue from the prior art in an obvious manner, are achieved by a process having the features of the present claim 1. Claims 2 to 9 are directed preferred embodiments of the present process.

Said object is achieved, in a manner which is extremely elegant and surprising but nonetheless advantageous for that, by, in a process for preparing enantiomerically enriched L-α-amino acids or their salts by reacting the corresponding 2-ketocarboxylic acid with an ammonium ion donor in the presence of a whole-cell catalyst which comprises a cloned gene encoding a cofactor-dependent amino acid dehydrogenase and a cloned gene encoding an enzyme which regenerates the cofactor, metering, at a total input of substrate per reaction volume of ≧500 mM, the addition of the substrate such that the stationary concentration of 2-ketocarboxylic acid is less than 500 mM and the external addition of cofactor, based on the total input of substrate, corresponds to <0.0001 equivalents.

Surprisingly, it is possible, for example by using the whole-cell catalyst while at the same time metering in the substrate, to dispense with any addition of the expensive cofactor or, by means of making a minimal external addition (<0.0001 equivalents), to keep its concentration in a low range, with this helping to save on process input costs. By contrast, without this metering technology and when initially introducing substrate quantities per reaction volumes of >500 mm, the reductive amination using the whole-cell catalyst only succeeds when relatively large quantities of the NAD+ cofactor are added. In the absence of the latter, the concentration only proceeds unsatisfactorily (see comparative example "synthesis example 1", initial substrate quantity per reaction volumes 900 mm—final turnover 25%). It is consequently only by using the process according to the invention (see synthesis examples 2 to 5) that it is possible to be able to almost completely dispense with the external addition of the cofactor even when carrying out the synthesis with relatively high total turnover quantities per reaction volumes and consequently under conditions which make sense from the point of process economics.

In a preferred embodiment, the expensive cofactor is therefore only added in quantities which are such that a concentration of preferably <0.00005 equivalents, extremely preferably <0.00001 equivalents, based on the substrate, is maintained. Very particular preference is given to an embodiment in which no cofactor is added externally to the reaction mixture. In this case, therefore, no addition of the cofactors (e.g. NAD(H)) need take place at all, something which it was not possible to deduce in an obvious manner from the prior art.

Within the context of the reaction under consideration, the skilled person is free to choose the genes which encode a cofactor-dependent amino acid dehydrogenase and an enzyme which regenerates the cofactor, which genes are to be expressed by the whole-cell catalyst, as host organism. He will lean toward enzymes which are known from the prior art.

With regard to the amino acid dehydrogenase, suitable enzymes are, in particular, those which are selected from the group consisting of leucine dehydrogenases (like in U.S. Pat. No. 5,854,035) and phenylalanine dehydrogenases (like in U.S. Pat. No. 5,416,019). Amino acid dehydrogenases (the latter e.g. in A. Bommarius in: Enzyme Catalysis in Organic Synthesis (Eds.: K. Drauz and H. Waldmann), Volume III, Wiley-VCH, Weinheim, 2002, chapter 15.3) which have proved to be suitable are, in particular, the leucine dehydrogenases, with the leucine dehydrogenases from *Bacillus* strains, and, in this case, in particular, from *Bacillus sphaericus, Bacillus cereus* (Seq. ID No. 5) and *Bacillus stearothermophilus* being particularly suitable. Cofactor-regenerating enzymes which can be taken into consideration are those selected from the group consisting of formate dehydrogenases (like in EP1295937), malate dehydrogenases (like in PCT/EP/03/08631), lactate dehydrogenases and glucose dehydrogenases (the latter, by way of example, in A. Bommarius in: Enzyme Catalysis in Organic Synthesis (eds.: K. Drauz and H. Waldmann), Volume III, Wiley-VCH, Weinheim, 2002, p. 1473, 993, 994, 1037, 1038, 1054, 1126; Glucose dehydrogenase from *Bacillus subtilis* expressed in *Escherichia coli*. I: Purification, characterization and comparison with glucose dehydrogenase from *Bacillus megaterium*, Hilt W; Pfleiderer G; Fortnagel P Biochimica and biophysica acta (Jan. 29, 1991), 1076(2), 298-304). The use of a formate dehydrogenase from *Candida boidinii* or mutants resulting therefrom (like in EP1295937; Seq. ID No. 7), while employing a formate-containing component as substrate, has proved to be very particularly preferred.

In this connection, a whole-cell catalyst which comprises a leucine dehydrogenase and a formate dehydrogenase from *Candida boidinii* or mutants derived therefrom is particularly suitable.

The substrate spectrum which is converted by the whole-cell catalyst differs depending on the amino acid dehydrogenase which is employed. While the leucine dehydrogenase is more suitable for linear and branched aliphatically substituted 2-ketocarboxylic acids, the phenylalanine dehydrogenase is preferably used for aromatic substituted substrates. With regard to the use of leucine dehydrogenase in the whole-cell catalyst, it is preferably possible to employ and convert substrates of the general formula (II) possessing an aliphatic radical R

(II)

Substrates which possess bulky aliphatic radicals as R are particularly suitable. These R radicals are primarily those selected from the group consisting of 1-adamantyl, neopentyl and tert-butyl. For this reason, preference is given to a process in which use is made of 2-ketocarboxylic acids, or salts resulting therefrom, which yield amino acids of the general formula (I)

in which R is alkyl, in particular a space-filling branched alkyl group which exhibits a tertiary C atom and possesses 5-10 C atoms, for example tert-butyl, and substituted alkyls.

In principle, the skilled person is free to choose the manner in which he carries out the process according to the invention. In this connection, he will lean toward processes which are known from the prior art. These processes can be continuous or discontinuous. It is advantageous to meter the addition of the substrate in accordance with a fed batch process [see, for example, synthesis examples 2 and 4] or by continuously adding it [see, for example, synthesis example 3 and 5, respectively]. In both process variants, the substrate is added such that the stationary concentration of substrate is less than 500 mM.

It has turned out to be advantageous to use the 2-ketocarboxylic acid employed as substrate at a maximum stationary concentration of less than 450 mM, and very particularly preferably of less than 400 mM, during the reaction.

In the fed batch process, the substrate is added in portions, after given units of time and preferably as a substrate solution. The number of the substrate portions which are added is preferably between 3 and 15, very preferably between 5 and 9. The concentration of the added substrate solution should preferably be set high enough to achieve a total input of substrate per reaction volume which is as high as possible. Synthesis examples 2 and 4 provide examples of this fed batch process variant. In the case of the continuous process variant, the substrate is added continuously over a given period of time, preferably at a constant metering rate, with the substrate preferably being added in the form of a substrate solution. Synthesis example 3 provides an example of this continuous process variant.

All known cells are suitable for use as the whole-cell catalyst which comprises an amino acid dehydrogenase and an enzyme which is capable of regenerating the cofactor. Microorganisms which may be mentioned in this regard are organisms such as yeasts, such as *Hansenula polymorpha, Pichia* sp., *Saccharomyces cerevisiae*, prokaryotes, such as *E. coli* and *Bacillus subtilis*, or eukaryotes, such as mammalian cells, insect cells or plant cells. The methods for cloning are well-known to the skilled person (Sambrook, J.; Fritsch, E. F. and Maniatis, T. (1989), Molecular cloning: a laboratory manual, 2nd ed., Cold Spring Harbor Laboratory Press, New York). Preference is given to using *E. coli* strains for this purpose. Those which are very particularly preferred are: *E. coli* XL1 Blue, NM 522, JM101, JM109, JM105, RR1, DH5α, TOP 10-, HB101, BL21 codon plus, BL21 (DE3) codon plus, BL21, BL21 (DE3), MM294. Plasmids which can preferably be used to clone the gene construct containing the nucleic acid according to the invention into the host organism are likewise known to the skilled person (see also PCT/EP03/07148; see below).

Suitable plasmids or vectors are, in principle, all the versions which are available to the skilled person for this purpose. These plasmids and vectors can be found, for example, in Studier and coworkers (Studier, W. F.; Rosenberg A. H.; Dunn J. J.; Dubendroff J. W.; (1990), Use of the T7 RNA polymerase to direct expression of cloned genes, Methods Enzymol. 185, 61-89) or the brochures provided by the companies Novagen, Promega, New England Biolabs, Clontech or Gibco BRL. Other preferred plasmids and vectors can be found in: Glover, D. M. (1985), DNA cloning: a practical approach, Vol. I-III, IRL Press Ltd., Oxford; Rodriguez, R. L. and Denhardt, D. T. (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York. Plasmids which can very preferably be used to clone the gene constructs containing the nucleic acid sequences under consideration into the host organism are, or are based on: pUC18/19 (Roche Biochemicals), pKK-177-3H (Roche Biochemicals), pBTac2 (Roche Biochemicals), pKK223-3 (Amersham Pharmacia Biotech), pKK-233-3 (Stratagene or pET (Novagen).

In another embodiment of the process according to the invention, before it is used, the whole-cell catalyst is preferably pretreated such that the permeability of the cell membrane for the substrates and products is increased as compared with the intact system. In this connection, particular preference is given to a process in which the whole-cell catalyst is, for example, pretreated by being frozen and/or by being treated with toluene. The essential features of the process according to the invention are shown in scheme 2.

The substrates can be employed at an extraordinarily high concentration when using the present process, as has also been described in the prior art when using the individual enzymes. In the present case, it is advantageous to employ the 2-ketocarboxylic acid at a concentration of greater than 500 mM. It is also preferred to introduce the substrate into the reaction at concentrations of greater than 800 mM, preferably greater than 900 mM and very particularly preferably greater than 1000 mM. However, in the case of this embodiment, it is essential to add cofactor to the reaction mixture in order to achieve corresponding turnover rates.

If, however, it is wished, despite a high space-time yield being demanded, to use the whole-cell catalyst such that it does not become necessary to add the expensive cofactor externally, or only necessary to make an extremely small external addition of less than 0.0001 equivalents, the skilled person can then surprisingly achieve this by the metering, in accordance with the invention, of the substrate.

In the case of the present reaction, the procedure is preferably that the whole-cell catalyst and the ammonium ion donor are initially introduced in water. Any compound which is suitable to the skilled person for this purpose can be used as the ammonium ion donor. In particular, these ammonium ion donors are compounds which are selected from the group consisting of typical ammonium salts. Very particular preference is given to using ammonium formate when a formate dehydrogenase is selected as the cofactor regeneration system or the ammonium salt of the respective ketoacid. The reaction can be depicted very clearly by means of the following scheme 2.

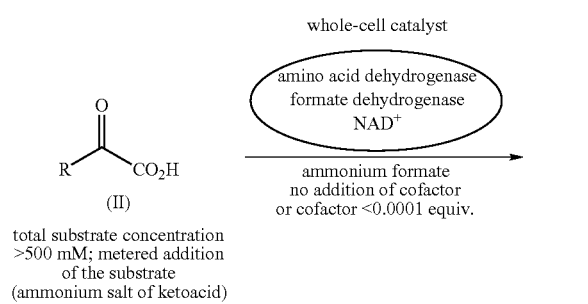

Scheme 2. Principle of the reaction in the whole-cell catalyst process according to the invention (taking as an example an NAD$^+$-dependent amino acid dehydrogenase and a formate dehydrogenase for regenerating cofactor)

In a further preferred embodiment the whole-cell catalyst embracing a glucose dehydrogenase and an amino acid dehydrogenase is mixed with water and glucose and the ammonium salt of the respective ketoacid is subjected thereto. The reaction is shown in subsequent

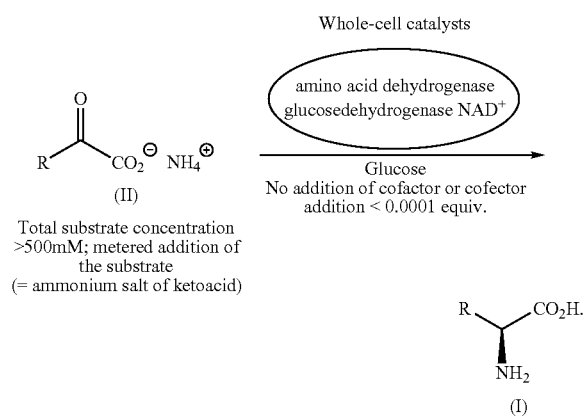

Scheme 3. Reaction of whole-cell catalyst of the invention, e.g. by way of an NAD$^+$-dependent amino acid dehydrogenase and a glucose dehydrogenase for regeneration of the cofactor.

If other dehydrogenases are used instead of the leucine dehydrogenase, the conditions under which the enzyme in question functions optimally can be found in the prior art. The reader is referred to U.S. Pat. No. 5,416,019 and Galkin et al. (Appl. Environ. Microbiol. 1997, 63, 4651) with regard to using a phenylalanine dehydrogenase.

With regard to the cofactor-regenerating enzymes and the conditions to be established, reference can be made to EP1295937 (formate dehydrogenase), PCT/EP/03/08631 (malate dehydrogenase) and Enzyme Catalysis in Organic Synthesis (Eds.: K. Drauz and H. Waldmann), Volume III, Wiley-VCH, Weinheim, 2002, S. 1473, 993, 994, 1037, 1038, 1054 or 1126. Further glucose dehydrogenase from *Bacillus subtilis* expressed in *E. coli* is preferred (I: Purification, characterization and comparison with glucose dehydrogenase from *Bacillus megaterium*, Hilt W; Pfleiderer G; Fortnagel P, Biochimica et biophysica acta (Jan. 29, 1991), 1076(2), 298-304) and literature cited therein.

The reaction mixture is worked up using methods known to the skilled person. In the batch process, the biomass can be readily separated from the product by means of filtration or centrifugation. The amino acid which is obtained can then be isolated using customary methods (ion exchange chromatography, crystallization).

However, the present process can also be carried out continuously. For this, the reaction is carried out in what is termed an enzyme-membrane reactor in which high molecular weight substances, i.e. the biomass, are retained behind an ultrafiltration membrane and low molecular weight substances, such as amino acids which have been produced, are able to pass through the membrane. A procedure of this nature has already been described several times in the prior art (Wandrey et al. in year-book 1998, Verfahrenstechnik und Chemieingenieurwesen [Process technology and chemical engineering], VDI, p. 151ff; Kragl et al., Angew. Chem. 1996, 6, 684).

The process, which is presented here, for preparing amino acids, which are, in particular, bulky, can very readily be established on a commercial scale on account of its advantages. The surprising fact that the addition, which is necessary in the case of the reaction under consideration, of a cofactor can be dispensed with in the process according to the invention, as well as the advantages arising from the fact that the whole-cell catalysts are easy to manage, constitute the nonobvious superiority of the present invention over the methods of the prior art.

Furthermore, it can be regarded as being surprising that the influence of undesirable metabolic/physiological functions is of no importance when using the whole-cell catalyst. Both aspects help, in an extraordinarily comprehensive manner, to lower the process costs entailed in preparing the L-α-amino acids.

It is furthermore surprising that, despite permeabilization of the cell wall and the possibility, associated therewith, of the cofactor present in the cells escaping, a negative impairment of the reaction which might be expected, for example as a result of the turnover being decreased, is not observed.

Within the context of the invention, optically enriched (enantiomerically enriched, enantiomer enriched, enantiomerically pure) compounds are understood as meaning the presence of one optical antipode at >50 mol % when mixed with the other.

The whole-cell catalyst is understood as meaning a microorganism which comprises cloned genes which encode enzymes which are at least able to catalyze two consecutive steps in the transformation of an organo-chemical compound. In this regard, and with regard to the general preparation methods (matching the enzyme expression with regard to the turnover rates), the reader is referred to EP1216304.

According to the invention, alkyl is understood as meaning a ($C_1$-$C_{18}$)-alkyl radical. This encompasses linear and arbitrarily branched radicals of this nature. It includes, in particular, methyl, ethyl, 1-propyl, 2-propyl, 1-n-butyl, 2-n-butyl, 1- or 2-isobutyl, 1- or 2-sec-butyl, tert-butyl, etc. The radicals can be substituted once or more than once by ($C_1$-$C_8$)-heteroalkyl radicals or radicals such as OH, SH, Hal and $NH_2$. Heteroalkyl radicals are understood as meaning, in particular, an alkyl radical as described above which possesses from 1 to 8 C atoms and which contains heteroatoms, such as O, S or N in its chain or which is bonded, by way of these heteroatoms, to the molecule under consideration.

External addition of cofactor means that this quantity of cofactor is added artificially to the reaction mixture. This quantity is to be seen as being in addition to the quantity of cofactor which is already inherently introduced into the reaction mixture by the whole-cell catalyst.

It goes without saying that the 2-ketocarboxylic acid which is used in the reaction is present in the reaction mixture in dissociated form. This form can be obtained either by using the ketocarboxylic acid and adjusting the pH correspondingly or by adding the salts of the ketocarboxylic acids. Both forms are included here analogously and in accordance with the invention.

The term total substrate concentration stands for the total input of substrate per reaction volume.

FIGURES

FIG. 1—pAM3.25 (Seq. ID No. 9):
Construction of pJOE4580.2

The plasmid pJOE4580.2 was formed from the published plasmid pJOE3075 (T. Stumpp, B. Wilms and J. Altenbuchner (2000) Biospektrum 1/2000: 33-36) by removing the malE gene by cutting with the restriction endonucleases NdeI/HindIII and replacing it with two oligonucleotides which once again complemented the NdeI and HindIII cleavage sites and, in addition to this, carried an NheI, an AatII and a PstI cleavage site. A SmaI fragment from the plasmid pJOE773 (J. Altenbuchner, P. Viell, I. Pelletier (1992) Positive selection vectors based on palindromic DNA sequences. Methods Enzymol 216: 457-466), which fragment carries the *E. coli* lacZalpha gene, was inserted into the NheI cleavage site after filling using Klenow polymerase and dNTPs. When harboring this plasmid, *E. coli* JM109 gives blue colonies on LB plates containing X-Gal and IPTG. This plasmid was named pJOE4580.2. The FDH sequence (Seq. ID No. 7) was cloned into this plasmid. The resulting plasmid was named pAM3.25.

Figure 2:
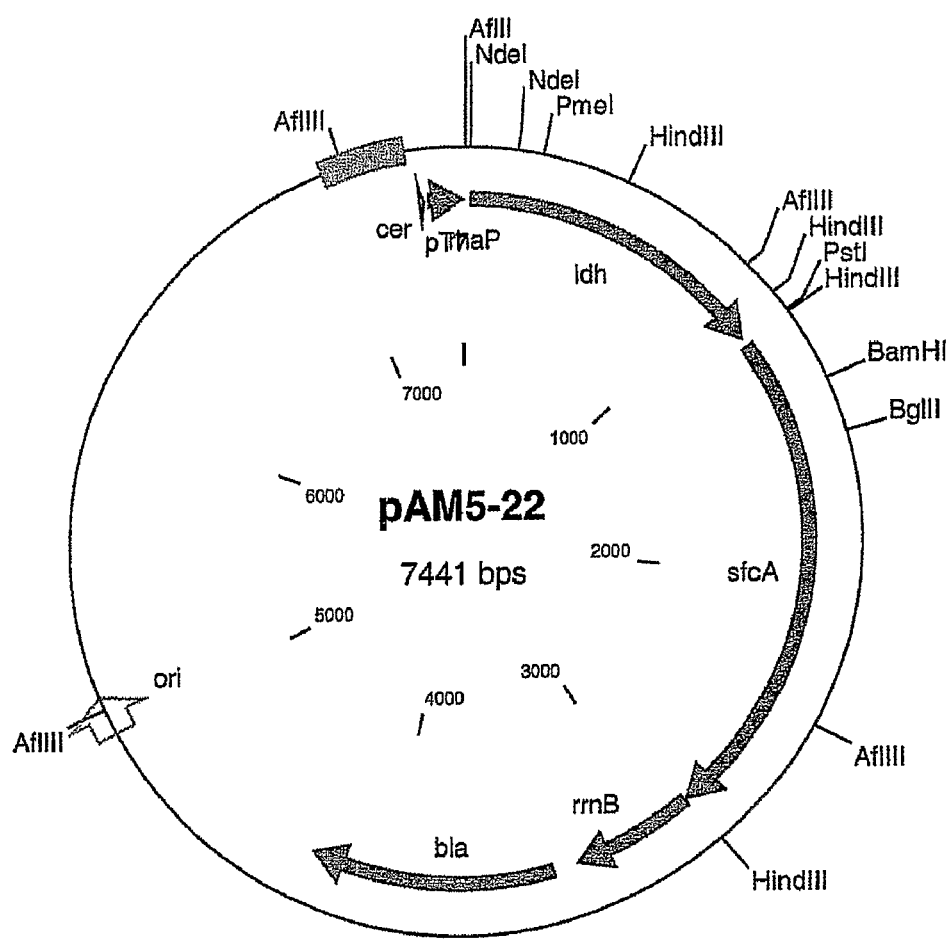

FIG. 2—pAM5.22
Construction of pJOE4580.2

The plasmid pJOE4580.2 was formed from the published plasmid pJOE3075 (T. Stumpp, B. Wilms and J. Altenbuchner (2000) Biospektrum 1/2000: 33-36) by removing the malE gene by cutting with the restriction endonucleases NdeI/HindIII and replacing it with two oligonucleotides which once again complemented the NdeI and HindIII cleavage sites and, in addition to this, carried an NheI, an AatII and a PstI cleavage site. A SmaI fragment from the plasmid pJOE773 (J. Altenbuchner, P. Viell, I. Pelletier (1992) Positive selection vectors based on palindromic DNA sequences. Methods Enzymol 216: 457-466), which fragment carries the *E. coli* lacZalpha gene, was inserted into the NheI cleavage site after filling using Klenow polymerase and dNTPs. When harboring this plasmid, *E. coli* JM109 gives blue colonies on LB plates containing X-Gal and IPTG. This plasmid was named pJOE4580.2. The LeuDH sequence (Seq. ID No. 5) was inserted into this plasmid. The new plasmid is named pAM5.22.

Figure 3:
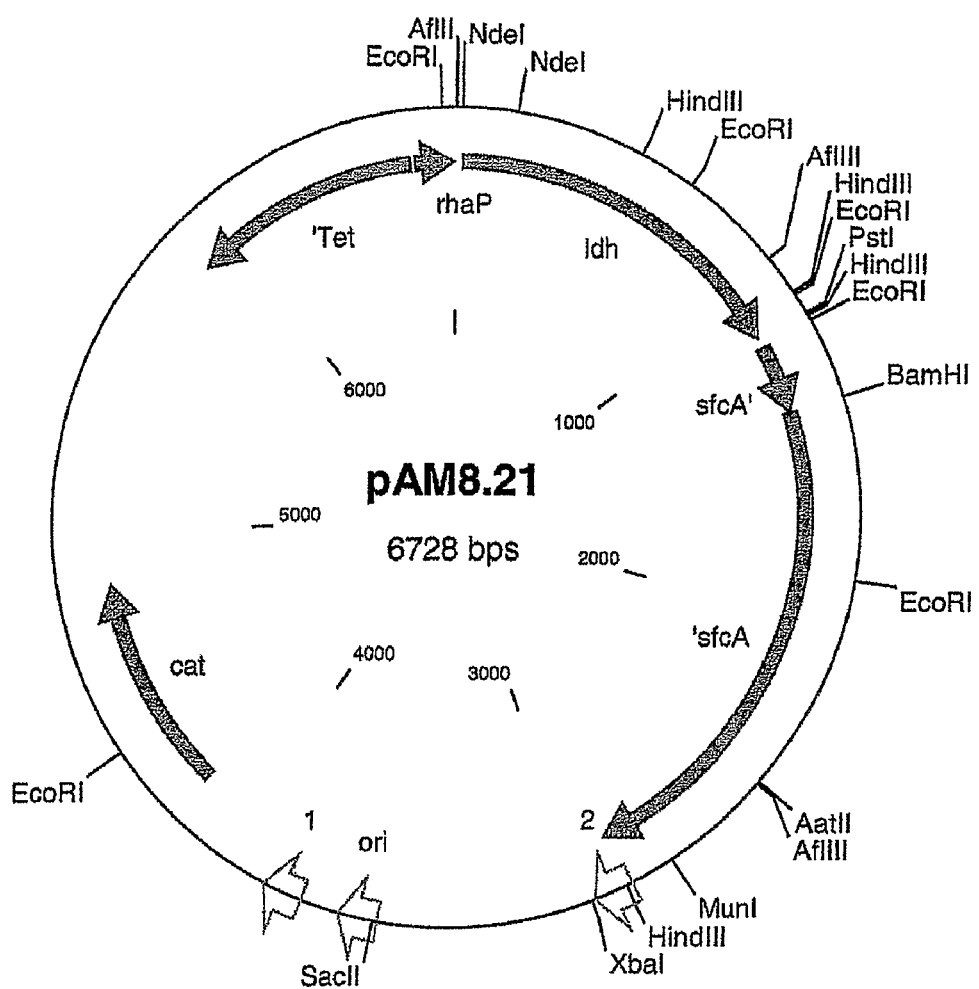

FIG. 3—pAM8.21
Construction of pHWG640.12 (Seq. ID No. 11)

Plasmid pHWG640.12 has not previously been published and its construction is therefore described as follows. This plasmid pHWG640.12 is constructed proceeding from the published plasmid pAW299 in a manner which is readily reworkable. Plasmid pAW299 is a pACYC184 derivative which contains a rhamnose promoter. Proceeding from pAW299 (B. Wilms, A. Wiese, C. Syldatk, R. Mattes, J. Altenbuchner (2001) J. Biotechnol 86: 19-30), the hyuC gene was excised from the plasmid with NdeI/HindIII and replaced with a PCR fragment which was cut with the same restriction enzymes and which contains the *E. coli* K12 sfcA (malic enzyme) gene. The resulting plasmid was designated pHWG640.12. The LeuDH sequence was inserted into this plasmid. The new plasmid is named pAM8.21.

Figure 4:
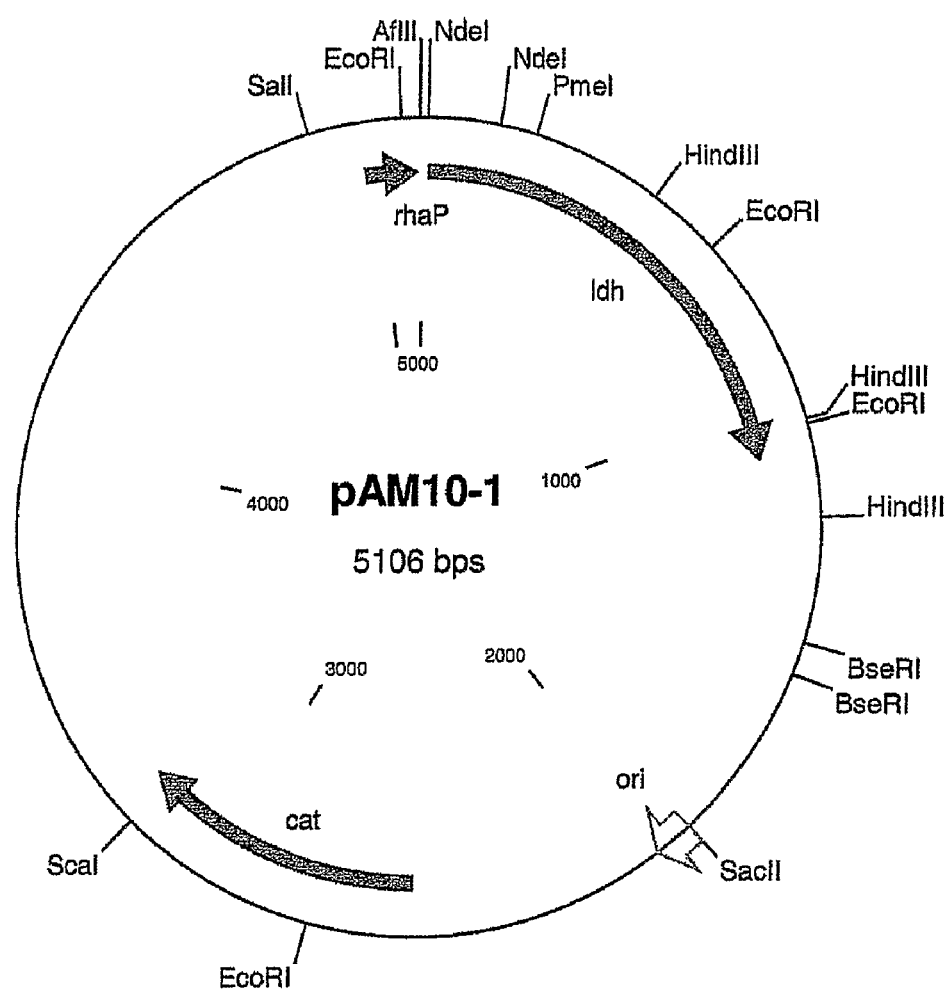

FIG. 4—pAM10.1 (Seq. ID No. 10)

The scfA gene (Seq. ID No. 11) was deleted from plasmid pAM8.21. The new plasmid is named pAM10.1.

FIG. 5

Biocatalyst with depiction of the course of the specific activity of leucine dehydrogenase (LeuDH) and formate dehydrogenase (FDH), and of the optical density, in dependence on the induction time; for a detailed description of the fermentation conditions, see experimental section.

Figure 6:
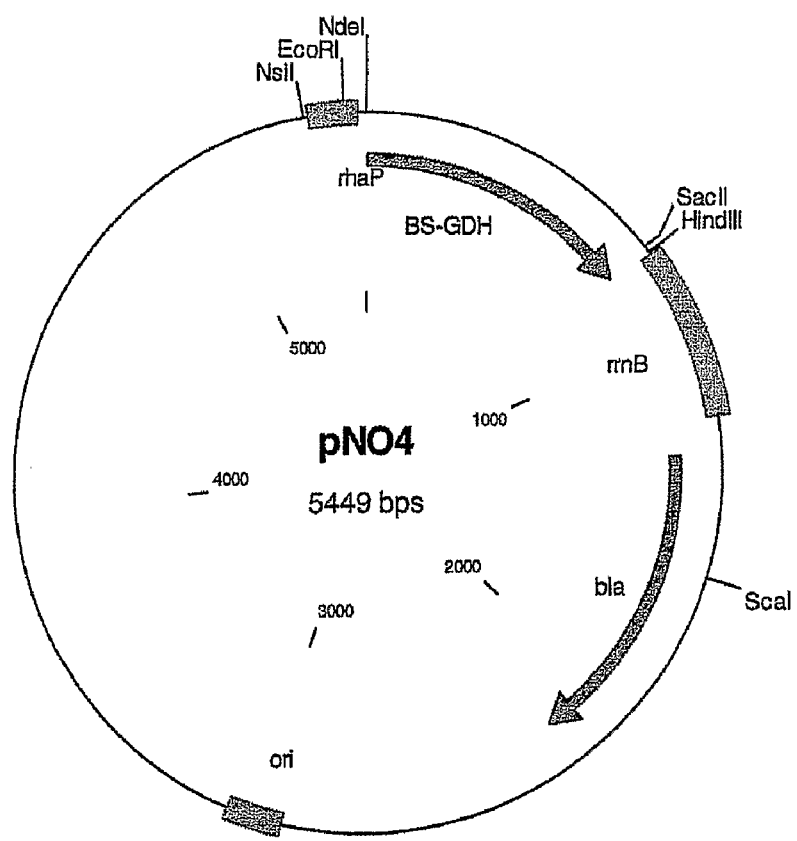

FIG. 6—pNO4 (Seq. ID No. 13)

The pAM10.1-transformed cells were then made chemically competent and transformed with plasmid pNO4. pNO4 carries a resistance to ampicillin (bla) and encodes a *Bacillus subtilis* glucose dehydrogenase.

EXPERIMENTAL EXAMPLES

Preparing the Whole-Cell Catalyst

Gene Amplification and Cloning

In order to clone the formate dehydrogenase (FDH, fdh3 from *Candida boidinii*, mutant with lower sensitivity to oxidation) and leucine dehydrogenase (*Bacillus cereus* LeuDH) for the whole-cell catalysis of the conversion of trimethylpyruvate into tert-leucine with regeneration of cofactor, the genes for the two enzymes were first of all amplified by PCR from chromosomal DNA obtained from the abovementioned strains. The oligonucleotides employed are listed in Table 1 while the composition of the PCR mixtures is given in Table 2 and the PCR program is given in Table 3.

TABLE 1

Oligonucleotides for amplifying the FDH and LeuDH genes

| Oligonucleotide | 5'-3' sequence | | Seq. ID No. |
|---|---|---|---|
| s3713 | AAA AAA CTT AAG AAG GAG ATA TAC ATA TGA CAT TAG AAA TCT TCG AA | LeuDH forward | 1 |
| s3714 | AAA AAA CTG CAG TTA GCG ACG GCT AAT AAT AT | LeuDH reverse | 2 |
| s3723 | AAA AAA CAT ATG AAG ATT GTC TTA GTT CTT | FDH forward | 3 |
| s3716 | AAA AAA GAC GTC TTA TTT CTT ATC GTG TTT ACC | FDH reverse | 4 |

The oligonucleotides were used to append cleavage sites for restriction endonucleases to the genes. These are BfrI in the case of s3713, PstI in the case of s3714, NdeI in the case of s3723 and AatII in the case of s3716 (see underlined regions).

TABLE 2

PCR mixtures, polymerase, buffer and $MgCl_2$ originate from the company Biomaster; the plasmid DNA starting concentration was 50 µg/ml

| Component | For FDH | Mixture for FDH | for LeuDH | Mixture for LeuDH |
|---|---|---|---|---|
| Plasmid DNA from strain FDH-C235/C262A | | 2 µl | pLeu2 plasmid DNA | 2 µl |
| 10X buffer | | 10 µl | | 10 µl |
| 50 mM MgCl2 | | 3 µl | | 3 µl |
| 100% DMSO | | 10 µl | | 10 µl |
| 10 mM dNTPs | | 2 µl | | 2 µl |
| 33 mM oligo 1 | S3723 | 1 µl | s3713 | 1 µl |
| 33 mM oligo 2 | s3716 | 1 µl | s3714 | 1 µl |
| Taq polymerase | | 1 µl | | 1 µl |
| Deionized H2O | | 70 µl | | 70 µl |

TABLE 3

PCR program: steps 2 to 4 were repeated 30 times

| Step | T, t for FDH amplification | T, t for LeuDH amplification |
|---|---|---|
| 1. Denaturation of the DNA | 94° C., 5 min | 94° C., 5 min |
| 2. Oligo annealing | 50° C., 1 min | 51° C., 1 min |
| 3. DNA elongation | 72° C., 1:30 min | 72° C., 1:30 min |
| 4. Denaturation of the dsDNA | 92° C., 1 min | 92° C., 1 min |
| 5. DNA elongation | 72° C., 7 min | 72° C., 7 min |

After the gene amplification, the PCR fragments were purified using the "DNA PCR and gel band purification kit" supplied by the company GFX and ligated into the L-rhamnose-inducible vectors pJOE4580.2 (pBR322 derivative; FIG. 1) and, respectively, pHWG640.12 (pACYC184 derivative; FIG. 3; Seq. ID No. 11) using the restriction endonucleases mentioned below.

In general, restriction mixtures were prepared using approx. 50 µg of DNA/ml in the 10 µl standard mixture. 1 µl of the first enzyme, and 1 µl of the 10× concentrated enzyme buffer, were also added. The mixtures were adjusted to the final volume using deionized H2O. The DNA to be inserted was incubated with the restriction enzymes separately from the plasmid DNA. After the restriction with the first enzyme, there then followed a precipitation step in which the DNA was precipitated with isopropanol and washed with ethanol and then dried and taken up in 8 µl of TE 10.01. In each case 1 µl of the second enzyme and 1 µl of the second 10× enzyme buffer were added to these mixtures, which were incubated once again at 37° C. for 1.5 h. The vector pAM10.1 was prepared from pAM8.21, this was also followed by a treatment with Klenow polymerase. The DNA was then separated into its fragments using a 1% agarose gel (Seakem agarose containing 0.4 µg of ethidium bromide/ml) and the correct bands were excised with a scalpel for further use. The DNA was eluted, in accordance with the instructions, from the small gel blocks using the "EASY PURE gel purification kit" supplied by the company Biozym and taken up in 15 µl TE 10.01.

For the ligation of vector and insert, the mixtures were selected such that the insert DNA was present at approximately twice the concentration of the target vector. In this case, too, the DNA concentration was approx. 50 µg/ml. The final volume of the ligation mixtures was 10 µl, with the mixtures also containing 1 µl of ligase and 1 µl of 10× concentrated ligase buffer (both from ROCHE) in addition to the vector/insert mixture. The incubation took place overnight at 4° C. The ligation mixtures were transformed into E. coli K12 JM109, with this bacterium then being selected on LB agar containing antibiotics (100 µg of ampicillin/ml (pAM3.25 [Seq. ID No. 9], pAM5.22) or 25 µg chloramphenicol/ml (pAM8.21, pAM10.1 [Seq. ID No. 10]), and clones were checked for the expected plasmid after the plasmids had been isolated.

Since LeuDH (Seq. ID No. 6) was initially to be coupled to malic enzyme (Seq. ID No. 12), the LeuDH gene was first of all inserted into pJOE4625.1, which already contained the gene for malic enzyme (sfcA) (FIG. 2). The LeuDH gene was then inserted into pHGW640.12 (FIG. 3), a pACYC184 derivative which also contained a rhamnose promoter and an sfcA gene, which latter was then deleted. The subcloning of the LeuDH gene from plasmid pAM5.22 (FIG. 2) into the target plasmid pAM10.1 (FIG. 4) was necessary in order to construct a two-plasmid system which requires two resistance markers for selection.

TABLE 4

Cloning results

| Gene/vector | Cloned into plasmid | Restriction with | New designation | FIG. |
|---|---|---|---|---|
| FDH PCR fragment | pJOE4580.2 | NdeI, AatII | pAM3.25 | 1 |
| LeuDH PCR fragment | pJOE4625.1 | BfrI, PstI | pAM5.22 | 2 |
| LeuDH from pAM5.22 | pHWG640.12 | BfrI, BamHI | pAM8.21 | 3 |
| pAM8.21 | Without sfcA gene | MunI, PstI | pAM10.1 | 4 |

Fermenting the Whole-Cell Catalyst

Figure 5:
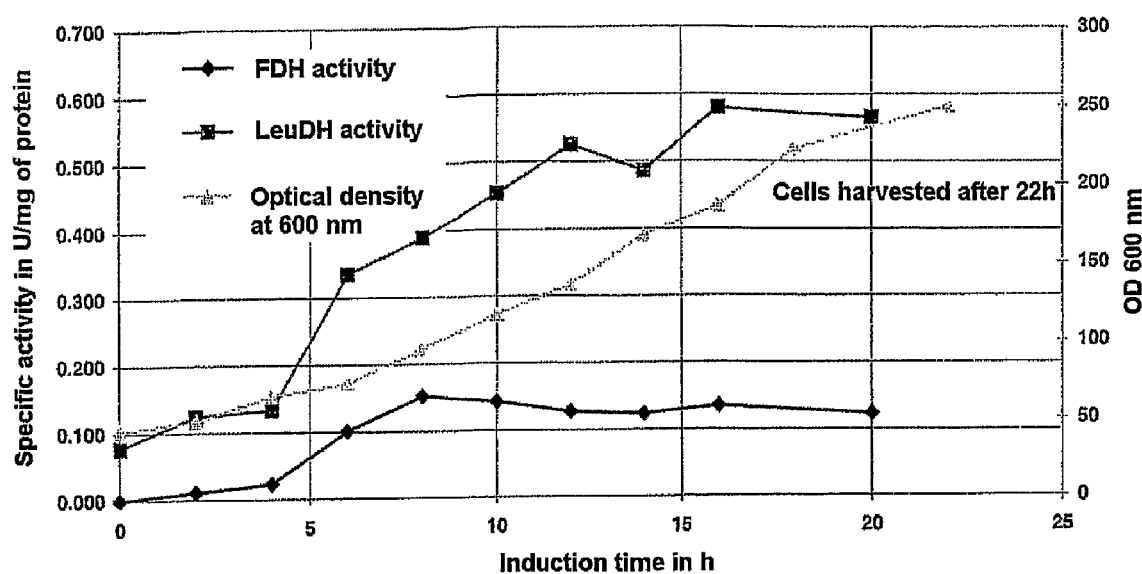

After HPLC analysis had shown that the FDH/LeuDH combination (E. coli JM109/pAM3.25/pAM10.1) achieved better results in converting trimethylpyruvate into tert-leucine than a comparative model system (malic enzyme/LeuDH on pAM5.22) in miniature-scale (1 ml) experiments in a thermoshaker, plasmids pAM3.25 and pAM10.1 were transformed into E. coli BW3110 since this strain is more suitable for fermentations. The intention was to use high cell density fermentation to prepare a sufficiently large biomass for all the following investigations using the model system. The fermentation was carried out without any antibiotic, with the preliminary cultures having been grown in the presence of antibiotic, at 30° C. in a 30 l fermenter containing a final volume of 8 l. For this, the cells were initially grown at 30° C. as a batch culture up to an OD600=50 and until the glucose had been completely consumed (approx. 22 h). Gene expression was then induced by adding rhamnose, which had been sterilized by filtration, to a final concentration of 0.2%, while fed batch culture was started by automatically adding nutrient solution and minerals (feed I and feed II). Samples, whose OD and enzyme activities were determined, using the respective activity tests in the latter case, were taken every two hours from the induction onward. The course of the OD, and of the activities, until fermentation was terminated are plotted against the time in FIG. 5.

The fermentation was terminated 22 h after the rhamnose induction since, despite increasing cell density, the activity of the FDH had stagnated and the cause of this was presumably plasmid loss or a reaction medium which was too acidic. The latter became apparent in the whole-cell reactions, in which the pH fell markedly (ΔpHmax=0.8), as compared with a previously pH-regulated solution, when the moist biomass was added. The activities of the two enzymes reached 0.565 U/mg of total protein in the case of the LeuDH and 0.123 U/mg of total protein in the case of the FDH. The volume activities, based on the fermentation medium, were 32.77 U/ml for the LeuDH and 7.14 U/ml for the FDH. After the medium had been removed in a separator, the cell yield was 1.4 kg of moist biomass. The cells were stored temporarily at −20° C. until being used as whole-cell catalyst.

| Fermentation media | |
|---|---|
| Preliminary culture: | 2 × 200 ml |
| Preliminary culture medium: | cNa2SO4 × 10H2O = 2 g/l |
| | c(NH4)2SO4 = 2.675 g/l |
| | cNH4Cl = 0.5 g/l |
| | cK2HPO4 = 14.625 g/l |
| | cNaH2PO4 × 2H2O = 3.6 g/l |
| | autoclave in 90% by vol. H2O |
| | cglucose = 10 g/l, final concentration |

(stock solution in H2O)
autoclave separately
1M MgSO4 solution, 2 ml/l
TES, 3 ml/l
Thiamine stock solution (10 g/l in H2O), 1 ml/l Batch culture: Add inoculum (380 ml in which Cx=12 g/l) containing glucose, MgSO4, TES and thiamine in an inoculation flask to the autoclaved batch medium Batch Medium (Quantity Taken for 8 l):

| | |
|---|---|
| Na2SO4 × 10H2O | 16 g |
| (NH4)2SO4 | 21.4 g |
| NH4Cl | 4 g |
| K2HPO4 | 117 g |
| NaH2PO4 × 2H2O | 28.8 g |
| (NH4) 2H-citrate | 8 g |
| dissolve in 7.5 l of H2O and sterilize in a 30 l fermenter | |
| Glucose monohydrate | 220 g |
| dissolve in 500 ml of H2O and autoclave (25 g/l) | |
| 1M MgSO4 solution | 16 ml |
| TES | 24 ml |
| Thiamine solution (10 g/l) | 8 ml |
| (sterilize the thiamine by filtration, autoclave the remainder) | |
| pH 7.2, using H3PO4 and NH3 | |

Fed Batch Feed:

| | | |
|---|---|---|
| I. | Glucose monohydrate autoclave | 2750 g in 3.5 l of H2O |
| | MgSO4 × 7H2O autoclave | 98.5 g in 0.15 l of H2O |
| | TES solution autoclave | 0.5 l |
| | Thiamine sterilize by filtration then combine in a feed flask | 2.5 g in 0.5 l of H2O |
| II. | (NH4)2HPO4 autoclave | 396 g in 1 l of H2O, pH 7 |

Feeds I and II are added using two separate pumps

| | |
|---|---|
| pH: | 7.2 (titrated with H3PO4 and NH3) |
| pO$_2$: | approx. 50 kPa (regulated by the rotational speed of the agitator) |

| Trace element solution (TES): | CaCl2 × 2H2O | 0.5 g |
|---|---|---|
| | ZnSO4 × 7H2O | 0.18 g |
| | MnSO4×H2O | 0.1 g |
| | Di-Na-EDTA | 20.1 g |
| | FeCl3 × 6H2O | 16.7 g |
| | CuSO4 × 5H2O | 0.16 g |
| | CoCl2 × 6H2O | 0.18 g |
| | H2O to 1 l | |

Preparing L-tert-leucine using a Whole-Cell Catalyst at 900 mM without Metering (Comparative Example=Synthesis Example 1)

50 ml of an 0.9 M solution of trimethylpyruvic acid (pH 7.0, adjusted with 32% ammonia), which also contains 1 mM magnesium chloride and 1% (v/v) toluene, are added to 5.85 g of the biocatalyst (*E. coli* JM105 (pAM 3.25_10.1) biomass) and 7.95 g of ammonium formate (2.8 mol equivalents). The pH is adjusted to pH 7.0 at the beginning of the reaction and not regulated any further after that, resulting in the pH rising during the reaction. The reaction temperature is 30° C. After a reaction time of 8 h, a conversion of 24.6% is measured, with it not being possible to increase this conversion any further even after an additional 15 h of stirring.

Preparing L-tert-leucine using a Whole-Cell Catalyst at Approx. 0.9 M and Employing Fed Batch Metering (Synthesis Example 2)

23.84 g of ammonium formate (corresponding to 2.8 equivalents based on the total substrate quantity employed) and 17.55 g of the biocatalyst (*E. coli* JM105 (pAM 3.25_10.1) biomass) are initially weighed into a 250 l three-neck flask, after which 28.50 ml of deionized water and 150 μl of a 1M solution of magnesium chloride (corresponding to a 1 mM concentration based on the final volume) are added. When the reaction temperature of 30° C. has been reached, the reaction is started by adding 7.50 ml of a 1.8 M solution of trimethylpyruvic acid (pH 7.0, adjusted with 32% ammonia). The pH is then adjusted to 7.0 by adding 32% ammonia. After that, in each case 7.50 ml of a 1.8 M solution of trimethylpyruvic acid (pH 7.0, adjusted with 32% ammonia) are firstly metered in twice after which different volumes of a 0.9 M solution of trimethylpyruvic acid (pH 7.0, adjusted with 32% ammonia) are metered in five times, with all the additions taking place at defined time intervals. The time intervals, and the quantities which are in each case metered in, are given in the following metering table. The final volume is 150 ml and the total concentration of added substrate is 0.86 M, corresponding to a volumetric quantity of trimethylpyruvic acid of 112.5 g/l. A complete conversion (>98% in accordance with HPLC) is observed after a reaction time of 24 h.

| Metering table Time (h) | Substrate solution ml (1.8 M) | Substrate solution ml (0.9 M) |
|---|---|---|
| 0 | 7.5 | 0 |
| 0.5 | 7.5 | 0 |
| 1 | 7.5 | 0 |
| 2.5 | 0 | 15 |
| 4 | 0 | 17.5 |
| 5.5 | 0 | 20 |
| 6.5 | 0 | 22.5 |
| 7 | 0 | 24 |
| Total volume of metered-in substrate solution | 22.5 | 99 |

Preparing L-tert-leucine using a Whole-Cell Catalyst at 1 M and Employing Continuous Metering (Synthesis Example 3)

26.48 g of ammonium formate (corresponding to 2.8 equivalents based on the total quantity of substrate employed), 150 µl of a 1 M solution of magnesium chloride (corresponding to a 1 mM concentration based on the final volume) and 19.49 g of the biocatalyst (*E. coli* JM105 (pAM3.25_10.1) biomass) are initially weighed into a 250 ml three-neck flask, after which 30 ml of deionized water are added. The pH is then adjusted to 7.0 by adding 32% ammonia. After the reaction temperature of 30° C. has been reached, a total of 120 ml of a 1.25 M solution of trimethylpyruvic acid (pH 7.0, adjusted with 32% ammonia) are added continuously at a flow rate of 0.2 ml/min over a period of 10 hours. The final volume is 150 ml and the total concentration of substrate employed is 1.0 M, corresponding to a volumetric quantity of trimethylpyruvic acid of 130.1 g/l. A conversion of 96% (in accordance with HPLC) is observed after a reaction time of 27 h.

Preparing L-tert-leucine Using a Whole-Cell Catalyst at 700 mM and Employing Fed Batch Metering (Synthesis Example 4)

2.55 g of sodium formate (corresponds to 2.5 mol/l based on final volume) are initially added to a conically shaped 100 ml reaction flask belonging to a STAT Titrino 718, after which 15 µl of a 1 M solution of $MgCl_2$ (corresponds to a final concentration of 1 mM) and 4.5 ml of a 1 M solution of TMP (pH 7, adjusted with 25% ammonia), and also 1.5% by vol. of toluene (based on the final volume), are added. The volume is made up to 15 ml with deionized $H_2O$. The reaction temperature of 30° C. is kept stable, and controlled, by a closed-loop water circuit. 1 g of the biocatalyst moist biomass is resuspended in the substrate mixture and the pH is adjusted to 6.9 to 7 with 25% ammonia.

After pH 7.5 has been reached, 4.5 ml of the 1 M TMP solution (pH 7) are added repeatedly. In this connection, the pH falls by approx. $\Delta pH=0.3$. As soon as pH 7.5 is reached, 4.5 ml of 1 M TMP solution are added once again. The addition of said volume of TMP is repeated 10× until the pH does not fall any further when TMP is added. In addition, 4 ml of a 4 M solution of sodium formate (corresponds, without taking any reaction into consideration, to a concentration of 973 mm in the medium) are added in connection with the eighth addition of TMP. The final volume is 64 ml, with a volumetric final concentration (without taking the reaction into consideration) of trimethylpyruvic acid of 774 mM (100.6 g/l). Sodium formate is present in solution at a final concentration of 836 mM. HPLC showed that 92% of the trimethylpyruvic acid had been converted after only 6 h.

The concentrations of the two substrates at the different addition points are listed in Table 5 below.

| Time [t in min] | Concentration of trimethyl-pyruvic acid [mM] | Concentration of sodium formate [mM] | Second addition of sodium formate |
|---|---|---|---|
| 0 | 300 | 2500 | |
| 45 | 461.54 | 1923.08 | |
| 60 | 562.5 | 1562.5 | |
| 75 | 631.58 | 1315.79 | |
| 90 | 681.82 | 1136.36 | |
| 105 | 720 | 1000 | |
| 120 | 750 | 892.86 | |
| 135 | 774.19 | 806.45 | |
| 150 | 736.36 | 972.73 | x |
| 180 | 756.30 | 899.16 | |
| 210 | 773.44 | 835.94 | |

Preparing a Whole-Cell Catalyst which Comprises a *Bacillus cereus* Leucine Dehydrogenase and a *Bacillus subtilis* Glucose Dehydrogenase Strain Preparation Chemically competent *E. coli* DSM14459 (described in patent WO03/042412) cells were transformed with plasmid pAM10.1 (FIG. 4, Seq. ID No. 10) (Sambrook et al. 1989, Molecular cloning: A Laboratory Manual, 2nd Edition, Cold Spring Harbor Laboratory Press). This plasmid carries a resistance to chloramphenicol (cat) and encodes a *Bacillus cereus* leucine dehydrogenase (ldh) (Stoyan, Tanja; Recktenwald, Achim; Kula, Maria-Regina. Cloning, sequencing and overexpression of the leucinee dehydrogenase gene from Bacillus cereus. Journal of Biotechnology (1997), 54(1), 77-80). The pAM10.1-transformed cells were then made chemically competent (Sambrook et al., 1989, Molecular cloning: A Laboratory Manual, 2nd Edition, Cold Spring Harbor Laboratory Press) and transformed with plasmid pNO4 (FIG. 6, Seq. ID No. 13). pNO4 carries a resistance to ampicillin (b1a) and encodes a *Bacillus subtilis* glucose dehydrogenase (BS-GLUCOSE DEHYDROGENASE) (Glucose dehydrogenase from *Bacillus subtilis* expressed in *Escherichia coli*. I: Purification, characterization and comparison with glucose dehydrogenase from *Bacillus megaterium*. Hilt W; Pfleiderer G; Fortnagel P, Biochimica and biophysica acta (Jan. 29, 1991), 1076(2), 298-304). The genes for the leucine dehydrogenase and the glucose dehydrogenase are under the control of a rhamnose promoter (rhaP) (Stumpp, Tina; Wilms, Burkhard; Altenbuchner, Josef., A new L-rhamnose-inducible expression system for *Escherichia coli*. Biospektrum (2000), 6(1), 33-36).

Preparing Active Cells

A single colony of *E. coli* DSM14459 (pAM10.1, pNO4) was incubated, at 37° C. for 18 hours and with shaking (250 rpm), in 2 ml of LB medium (10 g of yeast extract/l, 5 g of tryptone/l, 10 g of NaCl/l) in the added presence of antibiotics (50 µg of ampicillin/l and 20 µg of chloramphenicol/ml). This culture was diluted 1:100 in fresh LB medium containing rhamnose (2 g/l) as inducer, added antibiotics (50 µg of ampicillin/l and 20 µg of chloramphenicol/ml) and 1 mM $ZnCl_2$, and incubated at 30° C. for 18 hours with shaking (250 rpm). The cells were centrifuged (10 000 g, 10 min, 4° C.), after which the supernatant was discarded and the cell pellet was used in biotransformation experiments either directly or after having been stored at −20° C.

Preparing L-tert-leucine Using a Whole-Cell Catalyst at 1 M and Employing Continuous Metering (Synthesis Example 5)

9.98 g of the biocatalyst (*E. coli*-DSM 14459 (pAM 10.1, pNO4) biomass) are initially taken up in 30 ml of water in a 250 l three-neck flask, after which 32.70 g of D glucose are added. The pH is then adjusted to 7.0 by adding sodium hydroxide solution (25% strength) and kept constant at this value during the reaction (total consumption: 13.11 ml). After the reaction temperature of 30° C. has been reached, a total of 120 ml of a 1.25 M solution of trimethylpyruvic acid (pH 7.0, adjusted with 32% ammonia) are added continuously at a flow rate of 0.2 ml/min over a period of 10 hours. The final volume is approx. 165 ml and the total concentration of substrate employed is approx. 0.9 M, corresponding to a volumetric quantity of trimethylpyruvic acid of approx. 118 g/l. A conversion of >97% (according to HPLC), and an enantioselectivity of >99% ee for the product formed, are observed after a reaction time of 24 h.

The invention claimed is:

1. A process for preparing enantiomerically enriched L-α-amino acids or their salts, comprising reacting the corresponding 2-ketocarboxylic acid with an ammonium ion donor in the presence of a whole-cell catalyst comprising a cloned gene encoding a cofactor-dependent amino acid dehydrogenase and a cloned gene encoding glucose dehydrogenase that regenerates the cofactor, at a total input of substrate per reaction volume of ≧500 mM, the addition of the substrate being metered such that the stationary concentration of 2-ketocarboxylic acid is less than 500 mM and the external addition of cofactor, based on the total input of substrate, corresponds to <0.0001 equivalents.

2. The process as claimed in claim 1, wherein no cofactor is added to the reaction mixture.

3. The process as claimed in claim 1, wherein the 2 ketocarboxylic is one that will yield an amino acid of the general formula (I)

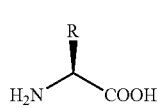

in which R is alkyl.

4. The process as claimed in claim 1, wherein the substrate is metered in accordance with a fed batch process.

5. The process as claimed in claim 1, wherein the 2-ketocarboxylic acid is kept at a maximum stationary concentration of less than 450 mM.

6. The process as claimed in claim 1, wherein before it is used, the whole-cell catalyst is pretreated such that the permeability of the cell membrane for the substrate and products is increased as compared with the intact system.

7. The process as claimed in claim 3, wherein R is a space-filling branched alkyl group that exhibits a tertiary C atom and possesses 5-10 carbon atoms.

8. The process as claimed in claim 7, wherein R is a tert-butyl or substituted alkyl.

9. The process as claimed in claim 5, wherein the 2-ketocarboxylic acid is kept at a maximum stationary concentration of less than 400 mM.

10. The process as claimed in claim 2, wherein the 2 ketocarboxylic is one that will yield an amino acid of the general formula (I)

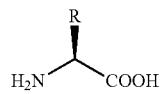

in which R is alkyl.

11. The process as claimed in claim 2, wherein the substrate is metered in accordance with a fed batch process.

12. The process as claimed in claim 2, wherein the 2-ketocarboxylic acid is kept at a maximum stationary concentration of less than 450 mM.

13. The process as claimed in claim 2, wherein before it is used, the whole-cell catalyst is pretreated such that the permeability of the cell membrane for the substrate and products is increased as compared with the intact system.

14. The process as claimed in claim 10, wherein R is a space-filling branched alkyl group that exhibits a tertiary C atom and possesses 5-10 carbon atoms.

15. The process as claimed in claim 14, wherein R is a tert-butyl or substituted alkyl.

16. The process as claimed in claim 12, wherein the 2-ketocarboxylic acid is kept at a maximum stationary concentration of less than 400 mM.

* * * * *

SEQUENCE LISTING

```
<160> NUMBER OF SEQ ID NOS: 13

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaaaactta agaaggagat atacatatga cattagaaat cttcgaa              47

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaaaactgc agttagcgac ggctaataat at                              32

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaaaaacata tgaagattgt cttagttctt                                 30

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaaaaagacg tcttatttct tatcgtgttt acc                             33

<210> SEQ ID NO 5
<211> LENGTH: 1120
<212> TYPE: DNA
<213> ORGANISM: Bacillus cereus
<220> FEATURE:
<221> NAME/KEY: CDS
<222> LOCATION: (20)..(1120)

<400> SEQUENCE: 5
ttaagaagga gatatacat atg aca tta gaa atc ttc gaa tac tta gaa aaa     52
                    Met Thr Leu Glu Ile Phe Glu Tyr Leu Glu Lys
```

```
                1               5                  10
tat gat tat gag caa gta gta ttt tgt caa gat aaa gaa tct ggt tta        100
Tyr Asp Tyr Glu Gln Val Val Phe Cys Gln Asp Lys Glu Ser Gly Leu
            15                  20                 25 aaa gca att att gca att cat gat aca aca ctt gga ccg gct ctt ggt        148
Lys Ala Ile Ile Ala Ile His Asp Thr Thr Leu Gly Pro Ala Leu Gly
        30                  35                  40 gga aca aga atg tgg aca tat gat tct gaa gaa gcg gcg att gaa gat        196
Gly Thr Arg Met Trp Thr Tyr Asp Ser Glu Glu Ala Ala Ile Glu Asp
    45                  50                  55 gca ttg cgt ctt gca aaa ggg atg aca tac aaa aac gca gca gct ggt        244
Ala Leu Arg Leu Ala Lys Gly Met Thr Tyr Lys Asn Ala Ala Ala Gly
60                  65                  70                  75 tta aac tta ggt ggt gcg aaa aca gta att atc ggt gat cct cgt aaa        292
Leu Asn Leu Gly Gly Ala Lys Thr Val Ile Ile Gly Asp Pro Arg Lys
                80                  85                  90 gat aag agc gaa gca atg ttc cgt gca cta gga cgt tat atc caa gga        340
Asp Lys Ser Glu Ala Met Phe Arg Ala Leu Gly Arg Tyr Ile Gln Gly
            95                  100                 105 cta aac gga cgt tac att aca gct gaa gat gtt ggt aca aca gta gat        388
Leu Asn Gly Arg Tyr Ile Thr Ala Glu Asp Val Gly Thr Thr Val Asp
        110                 115                 120 gat atg gat att atc cat gaa gaa act gac ttt gta aca ggt atc tca        436
Asp Met Asp Ile Ile His Glu Glu Thr Asp Phe Val Thr Gly Ile Ser
    125                 130                 135 cca tca ttc ggt tct tct ggt aac cca tct ccg gta act gca tac ggt        484
Pro Ser Phe Gly Ser Ser Gly Asn Pro Ser Pro Val Thr Ala Tyr Gly
140                 145                 150                 155 gtt tac cgt ggt atg aaa gca gct gca aaa gaa gct ttc ggt act gac        532
Val Tyr Arg Gly Met Lys Ala Ala Ala Lys Glu Ala Phe Gly Thr Asp
                160                 165                 170 aat tta gaa gga aaa gta att gct gtt caa ggc gtt ggt aac gta gca        580
Asn Leu Glu Gly Lys Val Ile Ala Val Gln Gly Val Gly Asn Val Ala
            175                 180                 185 tat cac cta tgc aaa cat tta cac gct gaa gga gca aaa tta att gtt        628
Tyr His Leu Cys Lys His Leu His Ala Glu Gly Ala Lys Leu Ile Val
        190                 195                 200 aca gat att aat aaa gaa gct gta caa cgt gct gta gaa gaa ttc ggt        676
Thr Asp Ile Asn Lys Glu Ala Val Gln Arg Ala Val Glu Glu Phe Gly
    205                 210                 215 gca tca gca gtt gaa cca aat gaa att tac ggt gtt gaa tgc gat att        724
Ala Ser Ala Val Glu Pro Asn Glu Ile Tyr Gly Val Glu Cys Asp Ile
220                 225                 230                 235 tac gca cca tgt gca cta ggc gca aca gtt aat gat gaa act att cca        772
Tyr Ala Pro Cys Ala Leu Gly Ala Thr Val Asn Asp Glu Thr Ile Pro
                240                 245                 250 caa ctt aaa gca aaa gta atc gca ggt tct gcg aat aac caa tta aaa        820
Gln Leu Lys Ala Lys Val Ile Ala Gly Ser Ala Asn Asn Gln Leu Lys
            255                 260                 265 gaa gat cgt cat ggt gac atc att cat gaa atg ggt att gta tac gca        868
Glu Asp Arg His Gly Asp Ile Ile His Glu Met Gly Ile Val Tyr Ala
        270                 275                 280 cca gat tat gta att aat gca ggt ggc gta att aac gta gca gac gaa        916
Pro Asp Tyr Val Ile Asn Ala Gly Gly Val Ile Asn Val Ala Asp Glu
    285                 290                 295 tta tat gga tac aat aga gaa cgt gca cta aaa cgt gtt gag tct att        964
Leu Tyr Gly Tyr Asn Arg Glu Arg Ala Leu Lys Arg Val Glu Ser Ile
300                 305                 310                 315 tat gac acg att gca aaa gta atc gaa att tca aaa cgc gat ggc ata       1012
Tyr Asp Thr Ile Ala Lys Val Ile Glu Ile Ser Lys Arg Asp Gly Ile
```

-continued

```
                320                 325                 330 gca act tat gta gcg gca gat cgt cta gct gaa gag cgc att gca agc      1060
Ala Thr Tyr Val Ala Ala Asp Arg Leu Ala Glu Glu Arg Ile Ala Ser
            335                 340                 345 ttg aag aat tct cgt agc act tac tta cgc aac ggt cac gat att att      1108
Leu Lys Asn Ser Arg Ser Thr Tyr Leu Arg Asn Gly His Asp Ile Ile
        350                 355                 360 agc cgt cgc taa                                                      1120
Ser Arg Arg
    365

<210> SEQ ID NO 6
<211> LENGTH: 366
<212> TYPE: PRT
<213> ORGANISM: Bacillus cereus

<400> SEQUENCE: 6

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Leu Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
```

```
              305                 310                 315                 320
Lys Val Ile Glu Ile Ser Lys Arg Asp Gly Ile Ala Thr Tyr Val Ala
                    325                 330                 335

Ala Asp Arg Leu Ala Glu Glu Arg Ile Ala Ser Leu Lys Asn Ser Arg
                340                 345                 350

Ser Thr Tyr Leu Arg Asn Gly His Asp Ile Ile Ser Arg Arg
                355                 360                 365

<210> SEQ ID NO 7
<211> LENGTH: 1095
<212> TYPE: DNA
<213> ORGANISM: Candida boidinii
<220> FEATURE:
<221> NAME/KEY: CDS
<222> LOCATION: (1)..(1095)

<400> SEQUENCE: 7 atg aag att gtc tta gtt ctt tat gat gct ggt aag cac gct gct gat      48
Met Lys Ile Val Leu Val Leu Tyr Asp Ala Gly Lys His Ala Ala Asp
1               5                   10                  15 gaa gaa aaa tta tat ggt tct act gaa aat aaa tta ggt att gct aat      96
Glu Glu Lys Leu Tyr Gly Ser Thr Glu Asn Lys Leu Gly Ile Ala Asn
            20                  25                  30 tgg tta aaa gat caa ggt cat gaa cta att act act tct gat aaa gaa     144
Trp Leu Lys Asp Gln Gly His Glu Leu Ile Thr Thr Ser Asp Lys Glu
        35                  40                  45 ggt gaa aca agt gaa ttg gat aaa cat atc cca gat gct gat att atc     192
Gly Glu Thr Ser Glu Leu Asp Lys His Ile Pro Asp Ala Asp Ile Ile
    50                  55                  60 atc acc act cct ttc cat cct gct tat atc act aag gaa aga ctt gac     240
Ile Thr Thr Pro Phe His Pro Ala Tyr Ile Thr Lys Glu Arg Leu Asp
65                  70                  75                  80 aag gct aag aac tta aaa tta gtc gtt gtc gct ggt gtt ggt tct gat     288
Lys Ala Lys Asn Leu Lys Leu Val Val Val Ala Gly Val Gly Ser Asp
                85                  90                  95 cac att gat tta gat tat att aat caa aca ggt aag aaa atc tca gtc     336
His Ile Asp Leu Asp Tyr Ile Asn Gln Thr Gly Lys Lys Ile Ser Val
            100                 105                 110 ctg gaa gtt aca ggt tct aat gtt gtc tct gtt gct gaa cac gtt gtc     384
Leu Glu Val Thr Gly Ser Asn Val Val Ser Val Ala Glu His Val Val
        115                 120                 125 atg acc atg ctt gtc ttg gtt aga aat ttc gtt cca gca cat gaa caa     432
Met Thr Met Leu Val Leu Val Arg Asn Phe Val Pro Ala His Glu Gln
    130                 135                 140 att att aac cac gat tgg gag gtt gct gct atc gct aag gat gct tac     480
Ile Ile Asn His Asp Trp Glu Val Ala Ala Ile Ala Lys Asp Ala Tyr
145                 150                 155                 160 gat atc gaa ggt aaa act atc gct acc att ggt gct ggt aga att ggt     528
Asp Ile Glu Gly Lys Thr Ile Ala Thr Ile Gly Ala Gly Arg Ile Gly
                165                 170                 175 tac aga gtc ttg gaa aga tta ctc cca ttt aat cca aaa gaa tta tta     576
Tyr Arg Val Leu Glu Arg Leu Leu Pro Phe Asn Pro Lys Glu Leu Leu
            180                 185                 190 tac tac gat tat caa gct tta cca aaa gaa gct gaa gaa aaa gtt ggt     624
Tyr Tyr Asp Tyr Gln Ala Leu Pro Lys Glu Ala Glu Glu Lys Val Gly
        195                 200                 205 gct aga aga gtt gaa aat att gaa gaa tta gtt gct caa gct gat atc     672
Ala Arg Arg Val Glu Asn Ile Glu Glu Leu Val Ala Gln Ala Asp Ile
    210                 215                 220 gtt aca gtt aat gct cca tta cac gca ggt aca aaa ggt tta att aat     720
Val Thr Val Asn Ala Pro Leu His Ala Gly Thr Lys Gly Leu Ile Asn
```

```
                 225                 230                 235                 240
aag gaa tta tta tct aaa ttt aaa aaa ggt gct tgg tta gtc aat acc          768
Lys Glu Leu Leu Ser Lys Phe Lys Lys Gly Ala Trp Leu Val Asn Thr
                        245                 250                 255 gca aga ggt gct att gct gtt gct gaa gat gtt gca gca gct tta gaa          816
Ala Arg Gly Ala Ile Ala Val Ala Glu Asp Val Ala Ala Ala Leu Glu
                260                 265                 270 tct ggt caa tta aga ggt tac ggt ggt gat gtt tgg ttc cca caa cca          864
Ser Gly Gln Leu Arg Gly Tyr Gly Gly Asp Val Trp Phe Pro Gln Pro
            275                 280                 285 gct cca aag gat cac cca tgg aga gat atg aga aat aaa tat ggt gct          912
Ala Pro Lys Asp His Pro Trp Arg Asp Met Arg Asn Lys Tyr Gly Ala
        290                 295                 300 ggt aat gcc atg act cct cac tac tct ggt act act tta gac gct caa          960
Gly Asn Ala Met Thr Pro His Tyr Ser Gly Thr Thr Leu Asp Ala Gln
305                 310                 315                 320 aca aga tac gct gaa ggt act aaa aat att ttg gaa tca ttc ttt acc         1008
Thr Arg Tyr Ala Glu Gly Thr Lys Asn Ile Leu Glu Ser Phe Phe Thr
                325                 330                 335 ggt aaa ttt gat tac aga cca caa gat att atc tta tta aat ggt gaa         1056
Gly Lys Phe Asp Tyr Arg Pro Gln Asp Ile Ile Leu Leu Asn Gly Glu
            340                 345                 350 tac gtt act aaa gct tac ggt aaa cac gat aag aaa taa                     1095
Tyr Val Thr Lys Ala Tyr Gly Lys His Asp Lys Lys
        355                 360

<210> SEQ ID NO 8
<211> LENGTH: 364
<212> TYPE: PRT
<213> ORGANISM: Candida boidinii

<400> SEQUENCE: 8

Met Lys Ile Val Leu Val Leu Tyr Asp Ala Gly Lys His Ala Ala Asp
1               5                   10                  15

Glu Glu Lys Leu Tyr Gly Ser Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Glu Lys Val Gly
        195                 200                 205
```

```
Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Ala Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO 9
<211> LENGTH: 5686
<212> TYPE: DNA
<213> ORGANISM: Artificial Sequence
<220> FEATURE:
<223> OTHER INFORMATION: Description of Artificial Sequence: Synthetic
      Plasmid pAM3.25

<400> SEQUENCE: 9
tatgaagatt gtcttagttc tttatgatgc tggtaagcac gctgctgatg aagaaaaatt      60
atatggttct actgaaaata aattaggtat tgctaattgg ttaaaagatc aaggtcatga     120
actaattact acttctgata agaaggtgaa acaagtgaa ttggataaac atatcccaga     180
tgctgatatt atcatcacca ctccttccaa tcctgcttat atcactaagg aaagacttga     240
caaggctaag aacttaaaat tagtcgttgt cgctggtgtt ggttctgatc acattgattt     300
agattatatt aatcaaacag gtaagaaaat ctcagtcctg gaagttacag gttctaatgt     360
tgtctctgtt gctgaacacg ttgtcatgac catgcttgtc ttggttagaa atttcgttcc     420
agcacatgaa caaattatta accacgattg ggaggttgct gctatcgcta aggatgctta     480
cgatatcgaa ggtaaaacta tcgctaccat tggtgctggt agaattggtt acagagtctt     540
ggaaagatta ctcccattta atccaaaaga attattatac tacgattatc aagctttacc     600
aaaagaagct gaagaaaaag ttggtgctag aagagttgaa atattgaag aattagttgc     660 tcaagctgat atcgttacag ttaatgctcc attacacgca ggtacaaaag gtttaattaa     720
taaggaatta ttatctaaat ttaaaaaagg tgcttggtta gtcaataccg caagaggtgc     780
tattgctgtt gctgaagatg ttgcagcagc tttagaatct ggtcaattaa gaggttacgg     840
tggtgatgtt tggttcccac aaccagctcc aaaggatcac ccatggagag atatgagaaa     900
taaatatggt gctggtaatg ccatgactcc tcactactct ggtactactt tagacgctca     960
aacaagatac gctgaaggta ctaaaaatat tttggaatca ttctttaccg gtaaatttga    1020
ttacagacca caagatatta tcttattaaa tggtgaatac gttactaaag cttacggtaa    1080
acacgataag aaataagacg tcaagcttgg ctgttttggc ggatgagaga agattttcag    1140
```

```
cctgatacag attaaatcag aacgcagaag cggtctgata aaacagaatt tgcctggcgg    1200
cagtagcgcg gtggtcccac ctgacccat  gccgaactca gaagtgaaac gccgtagcgc    1260
cgatggtagt gtggggtctc cccatgcgag agtagggaac tgccaggcat caaataaaac    1320
gaaaggctca gtcgaaagac tgggcctttc gttttatctg ttgtttgtcg gtgaacgctc    1380
tcctgagtag gacaaatccg ccgggagcgg atttgaacgt tgcgaagcaa cggcccggag    1440
ggtggcgggc aggacgcccg ccataaactg ccaggcatca aattaagcag aaggccatcc    1500
tgacggatgg cctttttgcg tttctacaaa ctcttttgtt tattttttcta aatacattca    1560 aatatgtatc cgctcatgag acaataaccc tgataaatgc ttcaataata ttgaaaaagg    1620
aagagtatga gtattcaaca tttccgtgtc gcccttattc ccttttttgc ggcattttgc    1680
cttcctgttt ttgctcaccc agaaacgctg gtgaaagtaa aagatgctga agatcagttg    1740
ggtgcacgag tgggttacat cgaactggat ctcaacagcg gtaagatcct tgagagtttt    1800
cgccccgaag aacgttttcc aatgatgagc acttttaaag ttctgctatg tggcgcggta    1860
ttatcccgtg ttgacgccgg gcaagagcaa ctcggtcgcc gcatacacta ttctcagaat    1920
gacttggttg agtactcacc agtcacagaa aagcatctta cggatggcat gacagtaaga    1980
gaattatgca gtgctgccat aaccatgagt gataacactg cggccaactt acttctgaca    2040
acgatcggag gaccgaagga gctaaccgct tttttgcaca acatggggga tcatgtaact    2100
cgccttgatc gttgggaacc ggagctgaat gaagccatac caaacgacga gcgtgacacc    2160
acgatgcctg tagcaatggc aacaacgttg cgcaaactat taactggcga actacttact    2220
ctagcttccc ggcaacaatt aatagactgg atggaggcgg ataaagttgc aggaccactt    2280
ctgcgctcgg cccttccggc tggctggttt attgctgata atctggagcc ggtgagcgt    2340 gggtctcgcg gtatcattgc agcactgggg ccagatggta agccctcccg tatcgtagtt    2400
atctacacga cggggagtca ggcaactatg gatgaacgaa atagacagat cgctgagata    2460
ggtgcctcac tgattaagca ttggtaactg tcagaccaag tttactcata tatactttag    2520
attgatttaa aacttcattt ttaatttaaa aggatctagg tgaagatcct tttgataat    2580 ctcatgacca aaatccctta acgtgagttt tcgttccact gagcgtcaga ccccgtagaa    2640
aagatcaaag gatcttcttg agatcctttt tttctgcgcg taatctgctg cttgcaaaca    2700
aaaaaaccac cgctaccagc ggtggtttgt ttgccggatc aagagctacc aactcttttt    2760
ccgaaggtaa ctggcttcag cagagcgcag ataccaaata ctgtccttct agtgtagccg    2820
tagttaggcc accacttcaa gaactctgta gcaccgccta catacctcgc tctgctaatc    2880
ctgttaccag tggctgctgc cagtggcgat aagtcgtgtc ttaccgggtt ggactcaaga    2940
cgatagttac cggataaggc gcagcggtcg ggctgaacgg ggggttcgtg cacacagccc    3000
agcttggagc gaacgaccta caccgaactg agatacctac agcgtgagct atgagaaagc    3060
gccacgcttc ccgaagggag aaaggcggac aggtatccgg taagcggcag ggtcggaaca    3120
ggagagcgca cgagggagct tccaggggga aacgcctggt atctttatag tcctgtcggg    3180
tttcgccacc tctgacttga gcgtcgattt tgtgatgct cgtcaggggg gcggagccta    3240
tggaaaaacg ccagcaacgc ggccttttta cggttcctgg ccttttgctg gccttttgct    3300
cacatgttct ttcctgcgtt atcccctgat tctgtggata accgtattac cgcctttgag    3360
tgagctgata ccgctcgccg cagccgaacg accgagcgca gcgagtcagt gagcgaggaa    3420
gcggaagagc gcctgatgcg gtattttctc cttacgcatc tgtgcggtat ttcacaccgc    3480
atatatggtg cactctcagt acaatctgct ctgatgccgc atagttaagc cagtatacac    3540
```

```
tccgctatcg ctacgtgact gggtcatggc tgcgccccga cacccgccaa cacccgctga    3600
cgcgccctga cgggcttgtc tgctcccggc atccgcttac agacaagctg tgaccgtctc    3660
cgggagctgc atgtgtcaga ggttttcacc gtcatcaccg aaacgcgcga ggcagctgcg    3720
gtaaagctca tcagcgtggt cgtgaagcga ttcacagatg tctgcctgtt catccgcgtc    3780
cagctcgttg agtttctcca gaagcgttaa tgtctggctt ctgataaagc gggccatgtt    3840
aagggcggtt ttttcctgtt tggtcacttg atgcctccgt gtaagggga atttctgttc    3900
atggggtaa tgataccgat gaaacgagag aggatgctca cgatacgggt tactgatgat    3960
gaacatgccc ggttactgga acgttgtgag ggtaaacaac tggcggtatg gatgcggcgg    4020
gaccagagaa aaatcactca gggtcaatgc cagcgcttcg ttaatacaga tgtaggtgtt    4080
ccacagggta gccagcagca tcctgcgatg cagatccgga acataatggt gcagggcgct    4140
gacttccgcg tttccagact ttacgaaaca cggaaaccga agaccattca tgttgttgct    4200
caggtcgcag acgttttgca gcagcagtcg cttcacgttc gctcgcgtat cggtgattca    4260
ttctgctaac cagtaaggca accccgccag cctagccggg tcctcaacga caggagcacg    4320
atcatgcgca cccgtggcca ggacccaacg ctgcccgaga tgcgccgcgt gcggctgctg    4380
gagatggcgg acgcgatgga tatgttctgc caagggttgg tttgcgcatt cacagttctc    4440
cgcaagaatt gattggctcc aattcttgga gtggtgaatc cgttagcgag gtgccgccgg    4500
cttccattca ggtcgaggtg gcccggctcc atgcaccgcg acgcaacgcg gggaggcaga    4560
caaggtatag gcggcgcct acaatccatg ccaacccgtt ccatgtgctc gccgaggcgg    4620
cataaatcgc cgtgacgatc agcggtccag tgatcgaagt taggctggta agagccgcga    4680
gcgatccttg aagctgtccc tgatggtcgt catctacctg cctggacagc atggcctgca    4740
acgcgggcat cccgatgccg ccggaagcga gaagaatcat aatggggaag gccatccagc    4800
ctcgcgtcgc gaacgccagc aagacgtagc ccagcgcgtc ggccgccatg ccggcgataa    4860
tggcctgctt ctcgccgaaa cgtttggtgg cgggaccagt gacgaaggct tgagcgaggg    4920
cgtgcaagat tccgaatacc gcaagcgaca ggccgatcat cgtcgcgctc cagcgaaagc    4980
ggtcctcgcc gaaaatgacc cagagcgctg ccggcacctg tcctacgagt tgcatgataa    5040
agaagacagt cataagtgcg gcgacgatag tcatgccccg cgcccaccgg aaggagctga    5100
ctgggttgaa ggctctcaag ggcatcggtc gacgctctcc cttatgcgac tcctgcatta    5160
ggaagcagcc cagtagtagg ttgaggccgt tgagcaccgc cgccgcaagg aatggtgcat    5220
gctcgatggc tacgagggca gacagtaagt ggatttacca taatccctta attgtacgca    5280
ccgctaaaac gcgttcagcg cgatcacggc agcagacagg taaaaatggc aacaaaccac    5340
cctaaaaact gcgcgatcgc gcctgataaa ttttaaccgt atgaatacct atgcaaccag    5400
agggtacagg ccacattacc cccacttaat ccactgaagc tgccattttt catggtttca    5460
ccatcccagc gaagggccat gcatgcatcg aaattaatac gacgaaatta atacgactca    5520
ctatagggca attgcgatca ccacaattca gcaaattgtg aacatcatca cgttcatctt    5580
tccctggttg ccaatggccc attttcctgt cagtaacgag aaggtcgcga attcaggcgc    5640
tttttagact ggtcgtaatg aacaattctt aagaaggaga tataca    5686
```

<210> SEQ ID NO 10
<211> LENGTH: 5106
<212> TYPE: DNA
<213> ORGANISM: Artificial Sequence
<220> FEATURE:
<223> OTHER INFORMATION: Description of Artificial Sequence: Synthetic
       Plasmid pAM10.1

<400> SEQUENCE: 10

```
gaaggagata tacatatgac attagaaatc ttcgaatact tagaaaaata tgattatgag      60
caagtagtat tttgtcaaga taaagaatct ggtttaaaag caattattgc aattcatgat     120
acaacacttg gaccggctct tggtggaaca agaatgtgga catatgattc tgaagaagcg     180
gcgattgaag atgcattgcg tcttgcaaaa gggatgacat acaaaaacgc agcagctggt     240
ttaaacttag gtggtgcgaa aacagtaatt atcggtgatc ctcgtaaaga taagagcgaa     300
gcaatgttcc gtgcactagg acgttatatc caaggactaa acggacgtta cattacagct     360
gaagatgttg gtacaacagt agatgatatg gatattatcc atgaagaaac tgactttgta     420
acaggtatct caccatcatt cggttcttct ggtaacccat ctccggtaac tgcatacggt     480
gtttaccgtg gtatgaaagc agctgcaaaa gaagctttcg gtactgacaa tttagaagga     540
aaagtaattg ctgttcaagg cgttggtaac gtagcatatc acctatgcaa acatttacac     600
gctgaaggag caaaattaat tgttacagat attaataaag aagctgtaca acgtgctgta     660
gaagaattcg gtgcatcagc agttgaacca atgaaatttt acggtgttga atgcgatatt     720
tacgcaccat gtgcactagg cgcaacagtt aatgatgaaa ctattccaca acttaaagca     780
aaagtaatcg caggttctgc gaataaccaa ttaaaagaag atcgtcatgg tgacatcatt     840
catgaaatgg gtattgtata cgcaccagat tatgtaatta atgcaggtgg cgtaattaac     900
gtagcagacg aattatatgg atacaataga gaacgtgcac taaaacgtgt tgagtctatt     960
tatgacacga ttgcaaaagt aatcgaaatt tcaaaacgcg atggcatagc aacttatgta    1020
gcggcagatc gtctagctga agagcgcatt gcaagcttga agaattctcg tagcacttac    1080
ttacgcaacg gtcacgatat tattagccgt cgctaacgcg tttgcggttg caaaatggc     1140
gcagcagcaa ggcgtggcgg tgaaaacctc tgccgaagcc ctgcaacagg ccattgacga    1200
taatttctgg caagccgaat accgcgacta ccgccgtacc tccatctaaa gcttatcga    1260
tgataagctg tcaaacatga gaattacaac ttatatcgta tggggctgac ttcaggtgct    1320
acatttgaag agataaattg cactgaaatc tagaaatatt ttatctgatt aataagatga    1380
tcttcttgag atcgttttgg tctgcgcgta atctcttgct ctgaaaacga aaaaccgcc     1440
ttgcagggcg ttttttcgaa ggttctctga gctaccaact cttgaaccg aggtaactgg     1500
cttggaggag cgcagtcacc aaaacttgtc ctttcagttt agccttaacc ggcgcatgac    1560
ttcaagacta actcctctaa atcaattacc agtggctgct gccagtggtg cttttgcatg    1620
tctttccggg ttggactcaa gacgatagtt accggataag gcgcagcggt cggactgaac    1680
gggggggttcg tgcatacagt ccagcttgga gcgaactgcc tacccggaac tgagtgtcag    1740
gcgtggaatg agacaaacgc ggccataaca gcggaatgac accggtaaac cgaaaggcag    1800
gaacaggaga gcgcacgagg gagccgccag gggaaacgcc tggtatcttt atagtcctgt    1860
cgggtttcgc caccactgat ttgagcgtca gatttcgtga tgcttgtcag gggggcggag    1920
cctatggaaa aacggctttg ccgcggccct ctcacttccc tgttaagtat cttcctggca    1980
tcttccagga aatctccgcc ccgttcgtaa gcctttccg ctcgccgcag tcgaacgacc     2040
gagcgtagcg agtcagtgag cgaggaagcg gaatatatcc tgtatcacat attctgctga    2100
cgcaccggtg cagccttttt tctcctgcca catgaagcac ttcactgaca ccctcatcag    2160
tgccaacata gtaagccagt atacactccg ctagcgctga tgtccggcgg tgcttttgcc    2220
gttacgcacc accccgtcag tagctgaaca ggagggacag ctgatagaaa cagaagccac    2280
tggagcacct caaaaacacc atcatacact aaatcagtaa gttggcagca tcacccgacg    2340
```

```
cactttgcgc cgaataaata cctgtgacgg aagatcactt cgcagaataa ataaatcctg   2400
gtgtccctgt tgataccggg aagccctggg ccaacttttg gcgaaaatga gacgttgatc   2460
ggcacgtaag aggttccaac tttcaccata atgaaataag atcactaccg ggcgtatttt   2520
ttgagttatc gagattttca ggagctaagg aagctaaaat ggagaaaaaa atcactggat   2580
ataccaccgt tgatatatcc caatggcatc gtaaagaaca ttttgaggca tttcagtcag   2640
ttgctcaatg tacctataac cagaccgttc agctggatat tacggccttt ttaaagaccg   2700
taaagaaaaa taagcacaag ttttatccgg cctttattca cattcttgcc cgcctgatga   2760
atgctcatcc ggaattccgt atggcaatga aagacggtga gctggtgata tgggatagtg   2820
ttcacccttg ttacaccgtt ttccatgagc aaactgaaac gttttcatcg ctctggagtg   2880
aataccacga cgatttccgg cagtttctac acatatattc gcaagatgtg gcgtgttacg   2940
gtgaaaacct ggcctatttc cctaaagggt ttattgagaa tatgtttttc gtctcagcca   3000
atccctgggt gagtttcacc agttttgatt taaacgtggc caatatggac aacttcttcg   3060
cccccgtttt caccatgggc aaatattata cgcaaggcga caaggtgctg atgccgctgg   3120
cgattcaggt tcatcatgcc gtctgtgatg gcttccatgt cggcagaatg cttaatgaat   3180
tacaacagta ctgcgatgag tggcagggcg gggcgtaatt ttttttaaggc agttattggt   3240 gcccttaaac gcctggtgct acgcctgaat aagtgataat aagcggatga atggcagaaa   3300
ttcgaaagca aattcgaccc ggtcgtcggt tcagggcagg gtcgttaaat agccgcttat   3360
gtctattgct ggtttaccgg tttattgact accggaagca gtgtgaccgt gtgcttctca   3420
aatgcctgag gccagtttgc tcaggctctc cccgtggagg taataattga cgatatgatc   3480
atttattctg cctcccagag cctgataaaa acggttagcg cttcgttaat acagatgtag   3540
gtgttccaca gggtagccag cagcatcctg cgatgcagat ccggaacata atggtgcagg   3600
gcgcttgttt cggcgtgggt atggtggcag gccccgtggc cgggggactg ttgggcgctg   3660
ccggcacctg tcctacgagt tgcatgataa agaagacagt cataagtgcg gcgacgatag   3720
tcatgccccg cgcccaccgg aaggagctac cggacagcgg tgcggactgt tgtaactcag   3780
aataagaaat gaggccgctc atggcgttga ctctcagtca tagtatcgtg gtatcaccgg   3840
ttggttccac tctctgttgc gggcaacttc agcagcacgt aggggacttc cgcgtttcca   3900
gactttacga aacacggaaa ccgaagacca ttcatgttgt tgctcaggtc gcagacgttt   3960
tgcagcagca gtcgcttcac gttcgctcgc gtatcggtga ttcattctgc taaccagtaa   4020
ggcaaccccg ccagcctagc cgggtcctca acgacaggag cacgatcatg cgcacccgtg   4080
gccaggaccc aacgctgccc gagatgcgcc gcgtgcggct gctggagatg gcggacgcga   4140
tggatatgtt ctgccaaggg ttggtttgcg cattcacagt tctccgcaag aattgattgg   4200
ctccaattct tggagtggtg aatccgttag cgaggtgccg ccggcttcca ttcaggtcga   4260
ggtggcccgg ctccatgcac cgcgacgcaa cgcggggagg cagacaaggt ataggcggc   4320 gcctacaatc catgccaacc cgttccatgt gctcgccgag gcggcataaa tcgccgtgac   4380
gatcagcggt ccagtgatcg aagttaggct ggtaagagcc gcgagcgatc cttgaagctg   4440
tccctgatgg tcgtcatcta cctgcctgga cagcatggcc tgcaacgcgg gcatcccgat   4500
gccgccggaa gcgagaagaa tcataatggg gaaggccatc cagcctcgcg tcgcgaacgc   4560
cagcaagacg tagcccagcg cgtcggccgc catgccggcg ataatggcct gcttctcgcc   4620
gaaacgtttg gtggcgggac cagtgacgaa ggcttgagcg agggcgtgca agattccgaa   4680
taccgcaagc gacaggccga tcatcgtcgc gctccagcga aagcggtcct cgccgaaaat   4740
```

-continued

```
gacccagagc gctgccggca cctgtcctac gagttgcatg ataaagaaga cagtcataag    4800
tgcggcgacg atagtcatgc cccgcgccca ccggaaggag ctgactgggt tgaaggctct    4860
caagggcatc ggtcgacgct ctcccttatg cgactcctgc attaggaagc agcccagtag    4920
taggttgagg ccgttgagca ccgccgccgc aaggaatggt gcatgcatcg atcaccacaa    4980
ttcagcaaat tgtgaacatc atcacgttca tctttccctg gttgccaatg gcccattttc    5040
ctgtcagtaa cgagaaggtc gcgaattcag gcgcttttta gactggtcgt aatgaacaat    5100
tcttaa                                                              5106
```

<210> SEQ ID NO 11
<211> LENGTH: 5597
<212> TYPE: DNA
<213> ORGANISM: Unknown
<220> FEATURE:
<223> OTHER INFORMATION: Description of Unknown: Plasmid sequence
<220> FEATURE:
<221> NAME/KEY: CDS
<222> LOCATION: (25)..(1749)
<223> OTHER INFORMATION: scfA-malic enzyme gene

<400> SEQUENCE: 11

```
aattcttaag aaggagatat acat atg gat att caa aaa aga gtg agt gac        51
                            Met Asp Ile Gln Lys Arg Val Ser Asp
                             1               5 atg gaa cca aaa aca aaa aaa cag cgt tcg ctt tat atc cct tac gct       99
Met Glu Pro Lys Thr Lys Lys Gln Arg Ser Leu Tyr Ile Pro Tyr Ala
 10              15                  20                  25 ggc cct gta ctg ctg gaa ttt ccg ttg ttg aat aaa ggc agt gcc ttc      147
Gly Pro Val Leu Leu Glu Phe Pro Leu Leu Asn Lys Gly Ser Ala Phe
                 30                  35                  40 agc atg gaa gaa cgc cgt aac ttc aac ctg ctg ggg tta ctg ccg gaa      195
Ser Met Glu Glu Arg Arg Asn Phe Asn Leu Leu Gly Leu Leu Pro Glu
             45                  50                  55 gtg gtc gaa acc atc gaa gaa caa gcg gaa cga gca tgg atc cag tat      243
Val Val Glu Thr Ile Glu Glu Gln Ala Glu Arg Ala Trp Ile Gln Tyr
         60                  65                  70 cag gga ttc aaa acc gaa atc gac aaa cac atc tac ctg cgt aac atc      291
Gln Gly Phe Lys Thr Glu Ile Asp Lys His Ile Tyr Leu Arg Asn Ile
 75                  80                  85 cag gac act aac gaa acc ctc ttc tac cgt ctg gta aac aat cat ctt      339
Gln Asp Thr Asn Glu Thr Leu Phe Tyr Arg Leu Val Asn Asn His Leu
 90                  95                 100                 105 gat gag atg atg cct gtt att tat acc cca acc gtc ggc gca gcc tgt      387
Asp Glu Met Met Pro Val Ile Tyr Thr Pro Thr Val Gly Ala Ala Cys
                110                 115                 120 gag cgt ttt tct gag atc tac cgc cgt tca cgc ggc gtg ttt atc tct      435
Glu Arg Phe Ser Glu Ile Tyr Arg Arg Ser Arg Gly Val Phe Ile Ser
            125                 130                 135 tac cag aac cgg cac aat atg gac gat att ctg caa aac gtg ccg aac      483
Tyr Gln Asn Arg His Asn Met Asp Asp Ile Leu Gln Asn Val Pro Asn
        140                 145                 150 cat aat att aaa gtg att gtg gtg act gac ggt gaa cgc att ctg ggg      531
His Asn Ile Lys Val Ile Val Val Thr Asp Gly Glu Arg Ile Leu Gly
155                 160                 165 ctt ggt gac cag ggc atc ggc ggg atg ggc att ccg atc ggt aaa ctg      579
Leu Gly Asp Gln Gly Ile Gly Gly Met Gly Ile Pro Ile Gly Lys Leu
170                 175                 180                 185 tcg ctc tat acc gcc tgt ggc ggc atc agc ccg gcg tat acc ctt ccg      627
Ser Leu Tyr Thr Ala Cys Gly Gly Ile Ser Pro Ala Tyr Thr Leu Pro
                190                 195                 200
```

```
gtg gtg ctg gat gtc gga acg aac aac caa cag ctg ctt aac gat ccg      675
Val Val Leu Asp Val Gly Thr Asn Asn Gln Gln Leu Leu Asn Asp Pro
            205                 210                 215 ctg tat atg ggc tgg cgt aat ccg cgt atc act gac gac gaa tac tat      723
Leu Tyr Met Gly Trp Arg Asn Pro Arg Ile Thr Asp Asp Glu Tyr Tyr
220                 225                 230 gaa ttc gtt gat gaa ttt atc cag gct gtg aaa caa cgc tgg cca gac      771
Glu Phe Val Asp Glu Phe Ile Gln Ala Val Lys Gln Arg Trp Pro Asp
    235                 240                 245 gtg ctg ttg cag ttt gaa gac ttt gct caa aaa aat gcg atg ccg tta      819
Val Leu Leu Gln Phe Glu Asp Phe Ala Gln Lys Asn Ala Met Pro Leu
250                 255                 260                 265 ctt aac cgc tat cgc aat gaa att tgt tct ttt aac gat gac att cag      867
Leu Asn Arg Tyr Arg Asn Glu Ile Cys Ser Phe Asn Asp Asp Ile Gln
                270                 275                 280 ggc act gcg gcg gta aca gtc ggc aca ctg atc gca gca agc cgc gcg      915
Gly Thr Ala Ala Val Thr Val Gly Thr Leu Ile Ala Ala Ser Arg Ala
            285                 290                 295 gca ggt ggt cag tta agc gag aaa aaa atc gtc ttc ctt ggc gca ggt      963
Ala Gly Gly Gln Leu Ser Glu Lys Lys Ile Val Phe Leu Gly Ala Gly
        300                 305                 310 tca gcg gga tgc ggc att gcc gaa atg atc atc tcc cag acc cag cgc     1011
Ser Ala Gly Cys Gly Ile Ala Glu Met Ile Ile Ser Gln Thr Gln Arg
    315                 320                 325 gaa gga tta agc gag gaa gcg gcg cgg cag aaa gtc ttt atg gtc gat     1059
Glu Gly Leu Ser Glu Glu Ala Ala Arg Gln Lys Val Phe Met Val Asp
330                 335                 340                 345 cgc ttt ggc ttg ctg act gac aag atg ccg aac ctg ctg cct ttc cag     1107
Arg Phe Gly Leu Leu Thr Asp Lys Met Pro Asn Leu Leu Pro Phe Gln
                350                 355                 360 acc aaa ctg gtg cag aag cgc gaa aac ctc agt gac tgg gat acc gac     1155
Thr Lys Leu Val Gln Lys Arg Glu Asn Leu Ser Asp Trp Asp Thr Asp
            365                 370                 375 agc gat gtg ctg tca ctg ctg gat gtg gtg cgc aat gta aaa cca gat     1203
Ser Asp Val Leu Ser Leu Leu Asp Val Val Arg Asn Val Lys Pro Asp
        380                 385                 390 att ctg att ggc gtc tca gga cag acc ggg ctg ttt acg gaa gag atc     1251
Ile Leu Ile Gly Val Ser Gly Gln Thr Gly Leu Phe Thr Glu Glu Ile
    395                 400                 405 atc cgt gag atg cat aaa cac tgt ccg cgt ccg atc gtg atg ccg ctg     1299
Ile Arg Glu Met His Lys His Cys Pro Arg Pro Ile Val Met Pro Leu
410                 415                 420                 425 tct aac ccg acg tca cgc gtg gaa gcc aca ccg cag gac att atc gcc     1347
Ser Asn Pro Thr Ser Arg Val Glu Ala Thr Pro Gln Asp Ile Ile Ala
                430                 435                 440 tgg acc gaa ggt aac gcg ctg gtc gcc acg ggc agc ccg ttt aat cca     1395
Trp Thr Glu Gly Asn Ala Leu Val Ala Thr Gly Ser Pro Phe Asn Pro
            445                 450                 455 gtg gta tgg aaa gat aaa atc tac cct atc gcc cag tgt aac aac gcc     1443
Val Val Trp Lys Asp Lys Ile Tyr Pro Ile Ala Gln Cys Asn Asn Ala
        460                 465                 470 ttt att ttc ccg ggc atc ggc ctg ggt gtt att gct tcc ggc gcg tca     1491
Phe Ile Phe Pro Gly Ile Gly Leu Gly Val Ile Ala Ser Gly Ala Ser
    475                 480                 485 cgt atc acc gat gag atg ctg atg tcg gca agt gaa acg ctg gcg cag     1539
Arg Ile Thr Asp Glu Met Leu Met Ser Ala Ser Glu Thr Leu Ala Gln
490                 495                 500                 505 tat tca cca ttg gtg ctg aac ggc gaa ggt atg gta ctg ccg gaa ctg     1587
Tyr Ser Pro Leu Val Leu Asn Gly Glu Gly Met Val Leu Pro Glu Leu
                510                 515                 520
```

```
aaa gat att cag aaa gtc tcc cgc gca att gcg ttt gcg gtt ggc aaa    1635
Lys Asp Ile Gln Lys Val Ser Arg Ala Ile Ala Phe Ala Val Gly Lys
            525                 530                 535 atg gcg cag cag caa ggc gtg gcg gtg aaa acc tct gcc gaa gcc ctg    1683
Met Ala Gln Gln Gln Gly Val Ala Val Lys Thr Ser Ala Glu Ala Leu
        540                 545                 550 caa cag gcc att gac gat aat ttc tgg caa gcc gaa tac cgc gac tac    1731
Gln Gln Ala Ile Asp Asp Asn Phe Trp Gln Ala Glu Tyr Arg Asp Tyr
    555                 560                 565 cgc cgt acc tcc atc taa aagcttatcg atgataagct gtcaaacatg           1779
Arg Arg Thr Ser Ile
570 agaattacaa cttatatcgt atggggctga cttcaggtgc tacatttgaa gagataaatt   1839 gcactgaaat ctagaaatat tttatctgat taataagatg atcttcttga gatcgttttg   1899 gtctgcgcgt aatctcttgc tctgaaaacg aaaaaaccgc cttgcagggc ggttttttcga  1959 aggttctctg agctaccaac tctttgaacc gaggtaactg gcttggagga gcgcagtcac   2019 caaaacttgt cctttcagtt tagccttaac cggcgcatga cttcaagact aactcctcta   2079 aatcaattac cagtggctgc tgccagtggt gcttttgcat gtctttccgg gttggactca   2139 agacgatagt taccggataa ggcgcagcgg tcggactgaa cggggggttc gtgcatacag   2199 tccagcttgg agcgaactgc ctacccggaa ctgagtgtca ggcgtggaat gagacaaacg   2259 cggccataac agcggaatga caccggtaaa ccgaaaggca ggaacaggag agcgcacgag   2319 ggagccgcca ggggaaacgc ctggtatctt tatagtcctg tcgggtttcg ccaccactga   2379 tttgagcgtc agatttcgtg atgcttgtca gggggggcgga gcctatggaa aaacggcttt   2439 gccgcggccc tctcacttcc ctgttaagta tcttcctggc atcttccagg aaatctccgc   2499 cccgttcgta agccatttcc gctcgccgca gtcgaacgac cgagcgtagc gagtcagtga   2559 gcgaggaagc ggaatatatc ctgtatcaca tattctgctg acgcaccggt gcagcctttt   2619 ttctcctgcc acatgaagca cttcactgac accctcatca gtgccaacat agtaagccag   2679 tatacactcc gctagcgctg atgtccgcg gtgcttttgc cgttacgcac caccccgtca    2739 gtagctgaac aggagggaca gctgatagaa acagaagcca ctggagcacc tcaaaaacac   2799 catcatacac taaatcagta agttggcagc atcacccgac gcactttgcg ccgaataaat   2859 acctgtgacg gaagatcact tcgcagaata aataaatcct ggtgtccctg ttgataccgg   2919 gaagccctgg gccaacttt ggcgaaaatg agacgttgat cggcacgtaa gaggttccaa    2979 cttttcaccat aatgaaataa gatcactacc gggcgtattt tttgagttat cgagattttc   3039 aggagctaag gaagctaaaa tggagaaaaa aatcactgga tataccaccg ttgatatatc   3099 ccaatggcat cgtaaagaac attttgaggc atttcagtca gttgctcaat gtacctataa   3159 ccagaccgtt cagctggata ttacggcctt tttaaagacc gtaaagaaaa ataagcacaa   3219 gttttatccg gcctttattc acattcttgc ccgcctgatg aatgctcatc cggaattccg   3279 tatggcaatg aaagacggtg agctggtgat atgggatagt gttcacccct gttacaccgt   3339 tttccatgag caaactgaaa cgttttcatc gctctggagt gaataccacg acgatttccg   3399 gcagtttcta cacatatatt cgcaagatgt ggcgtgttac ggtgaaaacc tggcctattt   3459 ccctaaaggg tttattgaga atatgttttt cgtctcagcc aatccctggg tgagtttcac   3519 cagttttgat ttaaacgtgg ccaatatgga caacttcttc gcccccgttt tcaccatggg   3579 caaatattat acgcaaggcg acaaggtgct gatgccgctg gcgattcagg ttcatcatgc   3639 cgtctgtgat ggcttccatg tcggcagaat gcttaatgaa ttacaacagt actgcgatga   3699
```

```
gtggcagggc ggggcgtaat ttttttaagg cagttattgg tgcccttaaa cgcctggtgc    3759
tacgcctgaa taagtgataa taagcggatg aatggcagaa attcgaaagc aaattcgacc    3819
cggtcgtcgg ttcagggcag ggtcgttaaa tagccgctta tgtctattgc tggtttaccg    3879
gtttattgac taccggaagc agtgtgaccg tgtgcttctc aaatgcctga ggccagtttg    3939
ctcaggctct ccccgtggag gtaataattg acgatatgat catttattct gcctcccaga    3999
gcctgataaa aacggttagc gcttcgttaa tacagatgta ggtgttccac agggtagcca    4059
gcagcatcct gcgatgcaga tccggaacat aatggtgcag ggcgcttgtt tcggcgtggg    4119
tatggtggca ggccccgtgg ccgggggact gttgggcgct gccggcacct gtcctacgag    4179
ttgcatgata aagaagacag tcataagtgc ggcgacgata gtcatgcccc gcgcccaccg    4239
gaaggagcta ccggacagcg gtgcggactg ttgtaactca gaataagaaa tgaggccgct    4299
catggcgttg actctcagtc atagtatcgt ggtatcaccg gttggttcca ctctctgttg    4359
cgggcaactt cagcagcacg tagggacttc cgcgtttcc agactttacg aaacacggaa    4419
accgaagacc attcatgttt ttgctcaggt cgcagacgtt tgcagcagc agtcgcttca    4479 cgttcgctcg cgtatcggtg attcattctg ctaaccagta aggcaacccc gccagcctag    4539
ccgggtcctc aacgacagga gcacgatcat gcgcacccgt ggccaggacc aacgctgcc    4599 cgagatgcgc cgcgtgcggc tgctggagat ggcggacgcg atggatatgt tctgccaagg    4659
gttggtttgc gcattcacag ttctccgcaa gaattgattg gctccaattc ttggagtggt    4719
gaatccgtta gcgaggtgcc gccggcttcc attcaggtcg aggtggcccg gctccatgca    4779
ccgcgacgca acgcggggag gcagacaagg tatagggcgg cgcctacaat ccatgccaac    4839
ccgttccatg tgctcgccga ggcggcataa atcgccgtga cgatcagcgg tccagtgatc    4899
gaagttaggc tggtaagagc cgcgagcgat ccttgaagct gtccctgatg gtcgtcatct    4959
acctgcctgg acagcatggc ctgcaacgcg ggcatcccga tgccgccgga agcgagaaga    5019
atcataatgg ggaaggccat ccagcctcgc gtcgcgaacg ccagcaagac gtagcccagc    5079
gcgtcggccg ccatgccggc gataatggcc tgcttctcgc cgaaacgttt ggtggcggga    5139
ccagtgacga aggcttgagc gagggcgtgc aagattccga ataccgcaag cgacaggccg    5199
atcatcgtcg cgctccagcg aaagcggtcc tcgccgaaaa tgacccagag cgctgccggc    5259
acctgtccta cgagttgcat gataaagaag acagtcataa gtgcggcgac gatagtcatg    5319
ccccgcgccc accggaagga gctgactggg ttgaaggctc tcaagggcat cggtcgacgc    5379
tctcccttat gcgactcctg cattaggaag cagcccagta gtaggttgag gccgttgagc    5439
accgccgccg caaggaatgg tgcatgcatc gatcaccaca attcagcaaa ttgtgaacat    5499
catcacgttc atctttccct ggttgccaat ggcccatttt cctgtcagta acgagaaggt    5559
cgcgaattca ggcgcttttt agactggtcg taatgaac                            5597
```

<210> SEQ ID NO 12
<211> LENGTH: 574
<212> TYPE: PRT
<213> ORGANISM: Unknown
<220> FEATURE:
<223> OTHER INFORMATION: Description of Unknown: Plasmid sequence

<400> SEQUENCE: 12

Met Asp Ile Gln Lys Arg Val Ser Asp Met Glu Pro Lys Thr Lys Lys
1               5                   10                  15

Gln Arg Ser Leu Tyr Ile Pro Tyr Ala Gly Pro Val Leu Leu Glu Phe
            20                  25                  30

```
Pro Leu Leu Asn Lys Gly Ser Ala Phe Ser Met Glu Glu Arg Arg Asn
         35                  40                  45

Phe Asn Leu Leu Gly Leu Leu Pro Glu Val Val Glu Thr Ile Glu Glu
 50                  55                  60

Gln Ala Glu Arg Ala Trp Ile Gln Tyr Gln Gly Phe Lys Thr Glu Ile
 65                  70                  75                  80

Asp Lys His Ile Tyr Leu Arg Asn Ile Gln Asp Thr Asn Glu Thr Leu
                     85                  90                  95

Phe Tyr Arg Leu Val Asn Asn His Leu Asp Glu Met Met Pro Val Ile
            100                 105                 110

Tyr Thr Pro Thr Val Gly Ala Ala Cys Glu Arg Phe Ser Glu Ile Tyr
        115                 120                 125

Arg Arg Ser Arg Gly Val Phe Ile Ser Tyr Gln Asn Arg His Asn Met
    130                 135                 140

Asp Asp Ile Leu Gln Asn Val Pro Asn His Asn Ile Lys Val Ile Val
145                 150                 155                 160

Val Thr Asp Gly Glu Arg Ile Leu Gly Leu Gly Asp Gln Gly Ile Gly
                165                 170                 175

Gly Met Gly Ile Pro Ile Gly Lys Leu Ser Leu Tyr Thr Ala Cys Gly
            180                 185                 190

Gly Ile Ser Pro Ala Tyr Thr Leu Pro Val Val Leu Asp Val Gly Thr
        195                 200                 205

Asn Asn Gln Gln Leu Leu Asn Asp Pro Leu Tyr Met Gly Trp Arg Asn
    210                 215                 220

Pro Arg Ile Thr Asp Asp Glu Tyr Tyr Glu Phe Val Asp Glu Phe Ile
225                 230                 235                 240

Gln Ala Val Lys Gln Arg Trp Pro Asp Val Leu Leu Gln Phe Glu Asp
                245                 250                 255

Phe Ala Gln Lys Asn Ala Met Pro Leu Leu Asn Arg Tyr Arg Asn Glu
            260                 265                 270

Ile Cys Ser Phe Asn Asp Asp Ile Gln Gly Thr Ala Ala Val Thr Val
        275                 280                 285

Gly Thr Leu Ile Ala Ala Ser Arg Ala Ala Gly Gly Gln Leu Ser Glu
    290                 295                 300

Lys Lys Ile Val Phe Leu Gly Ala Gly Ser Ala Gly Cys Gly Ile Ala
305                 310                 315                 320

Glu Met Ile Ile Ser Gln Thr Gln Arg Glu Gly Leu Ser Glu Glu Ala
                325                 330                 335

Ala Arg Gln Lys Val Phe Met Val Asp Arg Phe Gly Leu Leu Thr Asp
            340                 345                 350

Lys Met Pro Asn Leu Leu Pro Phe Gln Thr Lys Leu Val Gln Lys Arg
        355                 360                 365

Glu Asn Leu Ser Asp Trp Asp Thr Asp Ser Asp Val Leu Ser Leu Leu
    370                 375                 380

Asp Val Val Arg Asn Val Lys Pro Asp Ile Leu Ile Gly Val Ser Gly
385                 390                 395                 400

Gln Thr Gly Leu Phe Thr Glu Glu Ile Ile Arg Glu Met His Lys His
                405                 410                 415

Cys Pro Arg Pro Ile Val Met Pro Leu Ser Asn Pro Thr Ser Arg Val
            420                 425                 430

Glu Ala Thr Pro Gln Asp Ile Ile Ala Trp Thr Glu Gly Asn Ala Leu
        435                 440                 445

Val Ala Thr Gly Ser Pro Phe Asn Pro Val Val Trp Lys Asp Lys Ile
```

```
                      450                 455                 460
Tyr Pro Ile Ala Gln Cys Asn Asn Ala Phe Ile Phe Pro Gly Ile Gly
465                 470                 475                 480

Leu Gly Val Ile Ala Ser Gly Ala Ser Arg Ile Thr Asp Glu Met Leu
                485                 490                 495

Met Ser Ala Ser Glu Thr Leu Ala Gln Tyr Ser Pro Leu Val Leu Asn
            500                 505                 510

Gly Glu Gly Met Val Leu Pro Glu Leu Lys Asp Ile Gln Lys Val Ser
        515                 520                 525

Arg Ala Ile Ala Phe Ala Val Gly Lys Met Ala Gln Gln Gln Gly Val
    530                 535                 540

Ala Val Lys Thr Ser Ala Glu Ala Leu Gln Gln Ala Ile Asp Asp Asn
545                 550                 555                 560

Phe Trp Gln Ala Glu Tyr Arg Asp Tyr Arg Arg Thr Ser Ile
                565                 570
```

<210> SEQ ID NO 13
<211> LENGTH: 5068
<212> TYPE: DNA
<213> ORGANISM: Artificial Sequence
<220> FEATURE:
<223> OTHER INFORMATION: Description of Artificial Sequence: Synthetic Plasmid

<400> SEQUENCE: 13

```
tatgtatccg gatttaaaag gaaaagtcgt cgctattaca ggagctgctt cagggctcgg      60
aaaggcgatg gccattcgct tcggcaagga gcaggcaaaa gtggttatca actattatag     120
taataaacaa gatccgaacg aggtaaaaga gaggtcatc aaggcgggcg gtgaagctgt      180
tgtcgtccaa ggagatgtca cgaaagagga agatgtaaaa aatatcgtgc aaacggcaat     240
taaggagttc ggcacactcg atattatgat taataatgcc ggtctgaaa atcctgtgcc      300
atctcacgaa atgccgctca aggattggga taaagtcatc ggcacgaact taacgggtgc    360
ctttttagga agccgtgaag cgattaaata tttcgtagaa aacgatatca agggaaatgt    420
cattaacatg tccagtgtgc acgaagtgat tccttggccg ttatttgtcc actatgcggc    480
aagtaaaggc gggataaagc tgatgacaga acattagcg ttggaatacg cgccgaaggg    540
cattcgcgtc aataatattg ggccaggtgc gatcaacacg ccaatcaatg ctgaaaaatt    600
cgctgaccct aaacagaaag ctgatgtaga agcatgatt ccaatgggat atatcggcga    660
accggaggag atcgccgcag tagcagcctg gcttgcttcg aaggaagcca gctacgtcac    720
aggcatcacg ttattcgcgg acggcggtat gacacaatat ccttcattcc aggcaggccg    780
cggttaatag tagaagcttc tgttttggcg gatgagagaa gattttcagc ctgatacaga    840
ttaaatcaga acgcagaagc ggtctgataa aacagaattt gcctggcggc agtagcgcgg    900
tggtcccacc tgaccccatg ccgaactcag aagtgaaacg ccgtagcgcc gatggtagtg    960
tggggtctcc ccatgcgaga gtagggaact gccaggcatc aaataaaacg aaaggctcag   1020
tcgaaagact gggcctttcg ttttatctgt tgtttgtcgg tgaacgctct cctgagtagg   1080
acaaatccgc cgggagcgga tttgaacgtt gcgaagcaac ggcccggagg gtggcgggca   1140
ggacgcccgc cataaactgc caggcatcaa attaagcaga aggccatcct gacggatggc   1200
cttttgcgt ttctacaaac tctttgttt attttttctaa atacattcaa atatgtatcc    1260
gctcatgaga caataaccct gataaatgct tcaataatat tgaaaaagga agagtatgag   1320
tattcaacat ttccgtgtcg cccttattcc ctttttgcg cattttgcc ttcctgtttt    1380
```

```
tgctcaccca gaaacgctgg tgaaagtaaa agatgctgaa gatcagttgg gtgcacgagt   1440
gggttacatc gaactggatc tcaacagcgg taagatcctt gagagttttc gccccgaaga   1500
acgttttcca atgatgagca cttttaaagt tctgctatgt ggcgcggtat tatcccgtgt   1560
tgacgccggg caagagcaac tcggtcgccg catacactat tctcagaatg acttggttga   1620
gtactcacca gtcacagaaa agcatcttac ggatggcatg acagtaagag aattatgcag   1680
tgctgccata accatgagtg ataacactgc ggccaactta cttctgacaa cgatcggagg   1740
accgaaggag ctaaccgctt ttttgcacaa catgggggat catgtaactc gccttgatcg   1800
ttgggaaccg gagctgaatg aagccatacc aaacgacgag cgtgacacca cgatgcctgt   1860
agcaatggca acaacgttgc gcaaactatt aactggcgaa ctacttactc tagcttcccg   1920
gcaacaatta atagactgga tggaggcgga taaagttgca ggaccacttc tgcgctcggc   1980
ccttccggct ggctggttta ttgctgataa atctggagcc ggtgagcgtg gtctcgcgg   2040 tatcattgca gcactggggc cagatggtaa gccctcccgt atcgtagtta tctacacgac   2100
ggggagtcag gcaactatgg atgaacgaaa tagacagatc gctgagatag gtgcctcact   2160
gattaagcat tggtaactgt cagaccaagt ttactcatat atactttaga ttgatttaaa   2220
acttcatttt taatttaaaa ggatctaggt gaagatcctt tttgataatc tcatgaccaa   2280
aatcccttaa cgtgagtttt cgttccactg agcgtcagac cccgtagaaa agatcaaagg   2340
atcttcttga tccttttttt tctgcgcgt aatctgctgc ttgcaaacaa aaaaaccacc   2400
gctaccagcg gtggtttgtt tgccggatca agagctacca actcttttc cgaaggtaac   2460 tggcttcagc agagcgcaga taccaaatac tgtccttcta gtgtagccgt agttaggcca   2520
ccacttcaag aactctgtag caccgcctac atacctcgct ctgctaatcc tgttaccagt   2580
ggctgctgcc agtggcgata gtcgtgtct taccgggttg gactcaagac gatagttacc   2640
ggataaggcg cagcggtcgg gctgaacggg gggttcgtgc acacagccca gcttggagcg   2700
aacgacctac accgaactga gatacctaca gcgtgagcta tgagaaagcg ccacgcttcc   2760
cgaagggaga aaggcggaca ggtatccggt aagcggcagg gtcggaacag gagagcgcac   2820
gagggagctt ccagggggaa acgcctggta tctttatagt cctgtcgggt ttcgccacct   2880
ctgacttgag cgtcgatttt tgtgatgctc gtcaggggg cggagcctat ggaaaaacgc   2940
cagcaacgcg gcctttttac ggttcctggc cttttgctgg ccttttgctc acatgttctt   3000
tcctgcgtta tcccctgatt ctgtggataa ccgtattacc gcctttgagt gagctgatac   3060
cgctcgccgc agccgaacga ccgagcgcag cgagtcagtg agcgaggaag cggaagagcg   3120
cctgatgcgg tattttctcc ttacgcatct gtgcggtatt tcacaccgca tatatggtgc   3180
actctcagta caatctgctc tgatgccgca tagttaagcc agtatacact ccgctatcgc   3240
tacgtgactg ggtcatggct gcgccccgac acccgccaac acccgctgac gcgccctgac   3300
gggcttgtct gctcccggca tccgcttaca gacaagctgt gaccgtctcc gggagctgca   3360
tgtgtcagag gttttcaccg tcatcaccga aacgcgcgag gcagctgcgg taaagctcat   3420
cagcgtggtc gtgaagcgat tcacagatgt ctgcctgttc atccgcgtcc agctcgttga   3480
gtttctccag aagcgttaat gtctggcttc tgataaagcg ggccatgtta agggcggttt   3540
tttcctgttt ggtcacttga tgcctccgtg taagggggga tttctgttca tgggggtaat   3600
gataccgatg aaacgagaga ggatgctcac gatacgggtt actgatgatg aacatgcccg   3660
gttactggaa cgttgtgagg gtaaacaact ggcggtatgg atgcggcggg accagagaaa   3720
aatcactcag ggtcaatgcc agcgcttcgt taatacagat gtaggtgttc cacagggtag   3780
```

```
ccagcagcat cctgcgatgc agatccggaa cataatggtg cagggcgctg acttccgcgt    3840
ttccagactt tacgaaacac ggaaaccgaa gaccattcat gttgttgctc aggtcgcaga    3900
cgttttgcag cagcagtcgc ttcacgttcg ctcgcgtatc ggtgattcat tctgctaacc    3960
agtaaggcaa ccccgccagc ctagccgggt cctcaacgac aggagcacga tcatgcgcac    4020
ccgtggccag gacccaacgc tgcccgagat gcgccgcgtg cggctgctgg agatggcgga    4080
cgcgatggat atgttctgcc aagggttggt ttgcgcattc acagttctcc gcaagaattg    4140
attggctcca attcttggag tggtgaatcc gttagcgagg tgccgccggc ttccattcag    4200
gtcgaggtgg cccggctcca tgcaccgcga cgcaacgcgg ggaggcagac aaggtatagg    4260
gcggcggcgc ctacaatcca tgccaacccg ttccatgtgc tcgccgaggc ggcataaatc    4320
gccgtgacga tcagcggtcc agtgatcgaa gttaggctgg taagagccgc gagcgatcct    4380
tgaagctgtc cctgatggtc gtcatctacc tgcctggaca gcatggcctg caacgcgggc    4440
atcccgatgc cgccggaagc gagaagaatc ataatgggga aggccatcca gcctcgcgtc    4500
gcgaacgcca gcaagacgta gcccagcgcg tcggccgcca tgccggcgat aatggcctgc    4560
ttctcgccga aacgtttggt ggcgggacca gtgacgaagg cttgagcgag ggcgtgcaag    4620
attccgaata ccgcaagcga caggccgatc atcgtcgcgc tccagcgaaa gcggtcctcg    4680
ccgaaaatga cccagagcgc tgccggcacc tgtcctacga gttgcatgat aaagaagaca    4740
gtcataagtg cggcgacgat agtcatgccc cgcgcccacc ggaaggagct gactgggttg    4800
aaggctctca agggcatcgg tcgacgctct cccttatgcg actcctgcat taggaagcag    4860
cccagtagta ggttgaggcc gttgagcacc gccgccgcaa ggaatggtgc atgcatcgat    4920
caccacaatt cagcaaattg tgaacatcat cacgttcatc tttccctggt tgccaatggc    4980
ccattttcct gtcagtaacg agaaggtcgc gaattcaggc gcttttttaga ctggtcgtaa    5040 tgaacaattc ttaagaagga gatataca                                        5068
```